US007851624B2

(12) United States Patent
Niddam-Hildesheim et al.

(10) Patent No.: US 7,851,624 B2
(45) Date of Patent: Dec. 14, 2010

(54) TRIOL FORM OF ROSUVASTATIN AND SYNTHESIS OF ROSUVASTATIN

(75) Inventors: Valerie Niddam-Hildesheim, Kadima (IL); Anna Balanov, Rehovot (IL); Irena Veinberg, Rehovot (IL)

(73) Assignee: Teva Pharamaceutical Industries Ltd., Petah Tiqva (IL)

( * ) Notice: Subject to any disclaimer, the term of this patent is extended or adjusted under 35 U.S.C. 154(b) by 491 days.

(21) Appl. No.: 12/075,848

(22) Filed: Mar. 13, 2008

(65) Prior Publication Data
US 2008/0269270 A1 Oct. 30, 2008

Related U.S. Application Data

(63) Continuation-in-part of application No. 11/520,295, filed on Sep. 12, 2006, now abandoned, which is a continuation-in-part of application No. 11/020,834, filed on Dec. 23, 2004, now abandoned.

(60) Provisional application No. 60/906,914, filed on Mar. 13, 2007, provisional application No. 60/918,466, filed on Mar. 15, 2007, provisional application No. 60/532,458, filed on Dec. 24, 2003, provisional application No. 60/547,715, filed on Feb. 24, 2004.

(51) Int. Cl.
*C07D 239/02* (2006.01)
*G01N 33/00* (2006.01)
(52) U.S. Cl. ...................... 544/297; 436/131
(58) Field of Classification Search ............... None
See application file for complete search history.

(56) References Cited

U.S. PATENT DOCUMENTS

| 4,231,938 | A | 11/1980 | Monaghan et al. |
| 4,346,227 | A | 8/1982 | Terahara et al. |
| 4,444,784 | A | 4/1984 | Hoffman et al. |
| 4,645,854 | A | 2/1987 | Verhoeven et al. |
| 4,739,073 | A | 4/1988 | Kathawala |
| 5,003,080 | A | 3/1991 | Butler et al. |
| 5,006,530 | A | 4/1991 | Angerbauer et al. |
| 5,177,080 | A | 1/1993 | Angerbauer et al. |
| 5,189,164 | A | 2/1993 | Kapa et al. |
| 5,202,029 | A | 4/1993 | Haytko et al. |
| 5,218,138 | A | 6/1993 | Chiu et al. |
| 5,260,440 | A | 11/1993 | Hirai et al. |
| 5,354,772 | A | 10/1994 | Kathawala |
| 5,354,879 | A | 10/1994 | Konoike et al. |
| 5,677,455 | A | 10/1997 | Harada et al. |
| 5,717,124 | A | 2/1998 | Harada et al. |
| 5,741,934 | A | 4/1998 | Sandler et al. |
| 5,856,336 | A | 1/1999 | Fujikawa et al. |
| 6,124,340 | A | 9/2000 | Horvath |
| RE37,314 | E | 8/2001 | Hirai et al. |
| 6,333,198 | B1 | 12/2001 | Edmeades et al. |
| 6,437,065 | B1 | 8/2002 | Ritter et al. |
| 6,696,479 | B2 | 2/2004 | Van Der Schaaf et al. |
| 6,777,552 | B2 | 8/2004 | Niddam-Hildesheim et al. |
| 6,835,838 | B2 | 12/2004 | Chen et al. |
| 6,858,618 | B2 | 2/2005 | Raza et al. |
| 7,208,623 | B2 | 4/2007 | Sedelmeier et al. |
| 7,232,920 | B2 | 6/2007 | Puthiaparampil et al. |
| 7,368,468 | B2 | 5/2008 | Lifshitz-Liron et al. |
| 7,396,927 | B2 | 7/2008 | Niddam-Hildesheim et al. |
| 7,414,140 | B2 | 8/2008 | Lifshitz-Liron et al. |
| 2002/0161021 | A1 | 10/2002 | Bosch et al. |
| 2003/0232989 | A1 | 12/2003 | Antons et al. |
| 2004/0249154 | A1 | 12/2004 | Chen et al. |
| 2005/0032884 | A1 | 2/2005 | Lifshitz-Liron et al. |
| 2005/0038114 | A1 | 2/2005 | Lifshitz-Liron et al. |
| 2005/0080134 | A1 | 4/2005 | Niddam-Hildesheim et al. |
| 2005/0159615 | A1 | 7/2005 | Lifshitz-Liron et al. |
| 2006/0258882 | A1 | 11/2006 | Niddam-Hildesheim et al. |
| 2007/0037979 | A1 | 2/2007 | Niddam-Hildesheim et al. |
| 2007/0179166 | A1 | 8/2007 | Niddam-Hildesheim et al. |
| 2007/0191436 | A1 | 8/2007 | Niddam-Hildesheim et al. |
| 2008/0091014 | A1 | 4/2008 | Huang |

FOREIGN PATENT DOCUMENTS

| CN | 1 733 737 | 2/2006 |
| CN | 1807417 | 7/2006 |
| CN | 1821242 | 8/2006 |
| CN | 1 872 841 | 12/2006 |
| CN | 1307187 C | 3/2007 |
| CN | 1 958 593 | 5/2007 |
| CN | 1958593 | 5/2007 |
| CZ | 298330 | 8/2007 |
| EP | 0 065 835 | 11/1985 |

(Continued)

OTHER PUBLICATIONS

Evans, et al., "Reduction of β-Hydroxy Ketones with Catecholborane. A Stereoselective Approach to the Synthesis of Syn 1,3-Diols", *J. Org. Chem.*, 1990, pp. 5190-5192, vol. 55 (18).
Greene, "Protective Groups in Organic Synthesis", John Wiley & Sons, Inc., 1981.
Hull, et al., "Quantification Of Rosuvastatin in Human Plasma By Automated Solid-Phase Extraction Using Tandem Mass Spectrometric Detection", *Journal of Chromatography B: Biomedical Sciences & Applications*, 2002, pp. 219-228, vol. 772, No. 2.
Loubinoux, et al., "The Enantioselective Synthesis of Simplified Southern-Half Fragments of Soraphen A", *Tetrahedron*, 1995, pp. 3549-3558, vol. 51, No. 12.
Ohrlein, et al., "Chemo-Enzymatic Approach to Statin Side-Chain Building Blocks", *Adv. Synth. Catal.*, 2003, pp. 713-715, vol. 345.
Reddy, et al., "Enantioselective Synthesis of β-Hydroxy δ-Lactones: A New Approach to the Synthetic Congeners of 3-Hydroxy-3-methylglutaryl Coenzyme A Reductase Inhibitors" *J. Org. Chem.*, 1991, pp. 5752-5754, vol. 56.

(Continued)

*Primary Examiner*—Paul A Zucker
(74) *Attorney, Agent, or Firm*—Kenyon & Kenyon LLP

(57) ABSTRACT

Provided is a rosuvastatin triol and its use as a reference standard for analysis of rosuvastatin. Also provided are methods for preparation of rosuvastatin.

53 Claims, 2 Drawing Sheets

FOREIGN PATENT DOCUMENTS

| | | |
|---|---|---|
| EP | 0 363 934 | 4/1990 |
| EP | 0 554 455 | 8/1993 |
| EP | 1 816 126 | 8/2007 |
| JP | 07 118233 | 5/1995 |
| WO | WO 03/004455 | 1/2003 |
| WO | WO 03/087112 | 10/2003 |
| WO | WO 03/097614 A | 11/2003 |
| WO | WO 2004/094343 | 11/2004 |
| WO | WO 2004/108691 | 12/2004 |
| WO | WO 2005/023778 | 3/2005 |
| WO | WO 2005/040134 A1 | 5/2005 |
| WO | WO 2005/056534 | 6/2005 |
| WO | WO 2005/077916 | 8/2005 |
| WO | WO 2006/067456 | 6/2006 |
| WO | WO 2006/091770 | 8/2006 |
| WO | WO 2007/007119 | 1/2007 |
| WO | WO 2007/017117 | 2/2007 |
| WO | WO 2007/040940 | 4/2007 |
| WO | WO 2007/041666 | 4/2007 |
| WO | WO 2007/099561 | 9/2007 |
| WO | WO 2008/044243 | 4/2008 |
| WO | WO 2008/053334 | 5/2008 |
| WO | WO 2008/059519 | 5/2008 |
| WO | WO 2008/065410 | 6/2008 |
| WO | WO 2008/072078 | 6/2008 |
| WO | WO 2008/093205 | 8/2008 |
| WO | WO 2008/096257 | 8/2008 |

OTHER PUBLICATIONS

Shao, et al., "Asymmetric Hydrogenation of 3,5-Dioxoesters Catalyzed by Ru-binap Complex: A Short Step Asymmetric Synthesis of 6-Substituted 5,6-dihydro-2-pyrones", *Tetrahedron*, 1993, pp. 1997-2010, vol. 49 (10).

Snyder, et al., *Introduction To Modem Liquid Chromatography*, 2$^{nd}$ ed., John Wiley & Sons: New York, 1979, pp. 549, 552, 571-572.

Strobel, et al., *Chemical Instrumentation: A Systematic Approach*, 3$^{rd}$ ed., Wiley & Sons: New York, 1989, pp. 391-393, 879, 894, 921, 922, 924-925, 953.

Szantay, et al., "Synthesis of Novel HMG-CoA Reductase Inhibitors, Naphthalene Analogs of Mevinolin", *Liebigs Ann. Chem.*, 1992, pp. 145-157.

Tempkin, et al., "Asymmetric Synthesis of 3,5-Dihydroxy-6(E)-heptenoate-containing HMG-CoA Reductase Inhibitors", *Tetrahedron*, 1997, pp. 10659-10670, vol. 53 (31).

Watanabe, Masamichi et al., "Synthesis and biological activity of methanesulfonamide pyrimidine- and N-methanesulfonyl pyrrole-substituted 3,5-dihydroxy-6-heptenoates, a novel series of HMG-CoA reductase inhibitors," *Bioorganic & Medicinal Chemistry*, 5(2), pp. 437-444, 1997.

Witztum, "Chapter 36: Drugs Used In The Treatment Of Hyperlipoproteinemias", *Goodman & Gilman's The Pharmacological Basis Of Therapeutics*, 9$^{th}$ ed., 1996, p. 879.

TRIOL TBRE NMR

| NUMBER ATOM | $^1$H NMR (CDCl$_3$) | $^{13}$C NMR (CDCl$_3$) | |
|---|---|---|---|
| | δ | δ | J(Hz) |
| 1 | | 172.17 | |
| 2 | 2.33 | 42.22 | |
| 3 | 4.19 | 69.35 | |
| 4 | 1.58, 1.34 | 40.93 | |
| 5 | 4.21 | 70.41 | |
| 6 | 2.29, 1.58 | 42.84 | |
| 7 | 5.31 | 66.12 | |
| 2' | | 157.23 | |
| 4' | | 165.06 | |
| 5' | | 125.07 | |
| 6' | | 178.04 | |
| 7' | 3.87 | 32.42 | |
| 8' | 1.33 | 22.29, 22.79 | |
| 9' | 3.53 | 33.08 | |
| 10' | 3.50 | 42.51 | |
| 1" | | 134.80 | 3 |
| 2",6" | 7.52 | 131.7 | 8 |
| 3",5" | 7.13 | 115.24 | 21 |
| 4" | | 163.24 | 249 |
| 7" | | 81.95 | |
| 8" | 1.46 | 28.09 | |

TRIOL FORM OF ROSUVASTIN AND SYNTHESIS OF ROSUVASTATIN

CROSS REFERENCE TO RELATED APPLICATIONS

This application claims the benefit of U.S. Provisional Application Nos. 60/906,914 filed on Mar. 13, 2007 and 60/918,466 filed on Mar. 15, 2007, and is a Continuation-In-Part (CIP) of U.S. application Ser. No. 11/520,295 filed on Sep. 12, 2006, now abandoned, which is a Continuation-In-Part (CIP) of U.S. Ser. No. 11/020,834 filed on Dec. 23, 2004, now abandoned, which claims the benefit of U.S. Provisional Application Nos. 60/532,458 filed on Dec. 24, 2003 and 60/547,715 filed on Feb. 24, 2004, the disclosures of which are incorporated by reference in their entirety herein.

FIELD OF THE INVENTION

The present invention relates to rosuvastatin triol and its use as a reference standard for analysis of rosuvastatin.

BACKGROUND OF THE INVENTION

Statins are currently the most therapeutically effective drugs available for reducing low-density lipoprotein (LDL) particle concentration in the blood stream of patients at risk for cardiovascular disease. Thus, statins are used in the treatment of hypercholesterolemia, hyperlipoproteinemia, and atherosclerosis. A high level of LDL in the bloodstream has been linked to the formation of coronary lesions that obstruct the flow of blood and can rupture and promote thrombosis. Goodman and Gilman, The Pharmacological Basis of Therapeutics, page 879 (9th Ed. 1996).

Statins inhibit cholesterol biosynthesis in humans by competitively inhibiting the 3-hydroxy-3-methyl-glutaryl-coenzyme A ("HMG-CoA") reductase enzyme. HMG-CoA reductase catalyzes the conversion of HMG to mevalonate, which is the rate-determining step in the biosynthesis of cholesterol. Decreased production of cholesterol causes an increase in the number of LDL receptors and corresponding reduction in the concentration of LDL particles in the bloodstream. Reduction in the LDL level in the bloodstream reduces the risk of coronary artery disease. J.A.M.A. 1984, 251, 351-74.

Currently available statins include lovastatin, simvastatin, pravastatin, fluvastatin, cerivastatin and atorvastatin. Lovastatin (disclosed in U.S. Pat. No. 4,231,938) and simvastatin (disclosed in U.S. Pat. No. 4,444,784) are administered in the lactone form. After absorption, the lactone ring is opened in the liver by chemical or enzymatic hydrolysis, and the active hydroxy acid is generated.

Pravastatin (disclosed in U.S. Pat. No. 4,346,227) is administered as the sodium salt. Fluvastatin (disclosed in U.S. Pat. No. 4,739,073) and cerivastatin (disclosed in U.S. Pat. Nos. 5,006,530 and 5,177,080), also administered as the sodium salt, are entirely synthetic compounds that are in part structurally distinct from the fungal derivatives of this class that contain a hexahydronaphthalene ring. Atorvastatin and two new "superstatins," rosuvastatin and pitavastatin, are administered as calcium salts.

Rosuvastatin calcium (monocalcium bis(+)7-[4-(4-fluorophenyl)-6-isopropyl-2-(N-methyl-N-methylsulfonylaminopyrimidin)-5-yl]-(3R,5S)-dihydroxy-(E)-6-heptanoate) is an HMG-CoA reductase inhibitor, developed by Shionogi for the once daily oral treatment of hyperlipidaemia (Ann Rep, Shionogi, 1996; Direct communications, Shionogi, 8 Feb. 1999 & 25 Feb. 2000). Rosuvastatin calcium has the following chemical formula:

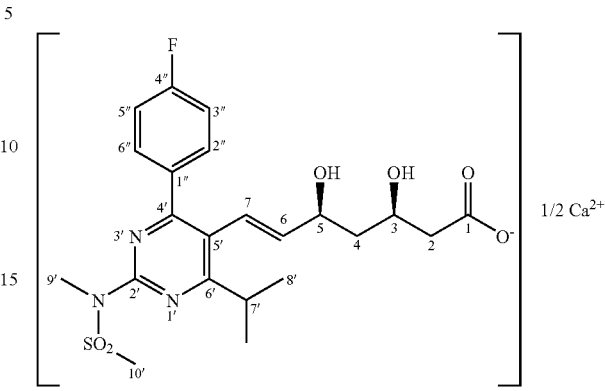

Rosuvastatin calcium is marketed under the name CRESTOR® for treatment of a mammal such as a human. According to the maker of CRESTOR®, it is administered in a daily dose of from about 5 mg to about 40 mg. For patients requiring less aggressive LDL-C reductions or who have pre-disposing factors for myopathy, the 5 mg dose is recommended, while 10 mg dose is recommended for the average patient, 20 mg dose for patients with marked hyper-cholesterolemia and aggressive lipid targets (>190 mg/dL), and the 40 mg dose for patients who have not been responsive to lower doses.

U.S. Pat. No. 5,260,440 discloses and claims rosuvastatin, its calcium salt (2:1), and its lactone form. The process of the '440 patent prepares rosuvastatin by reacting 4-(4-fluorophenyl)-6-isopropyl-2-(N-methyl-N-methylsulfonylamino)-5-pyrimidinecarbaldehyde with methyl (3R)-3-(tert-butyldimethylsilyloxy)-5-oxo-6-triphenylphosphoranylidene hexanoate in acetonitrile under reflux. The silyl group is then cleaved with hydrogen fluoride, followed by reduction with sodium borohydride ($NaBH_4$) and diethylmethoxyborane in tetrahydrofuran (THF) to obtain a methyl ester of rosuvastatin.

The ester is then hydrolyzed with sodium hydroxide (NaOH) in ethanol at room temperature, followed by removal of ethanol and addition of ether, to obtain the sodium salt of rosuvastatin. The sodium salt is then converted to the calcium salt. The sodium salt is dissolved in water and maintained under a nitrogen atmosphere. Calcium chloride is then added to the solution, resulting in precipitation of rosuvastatin calcium (2:1). The process for preparation of the intermediates disclosed in the '440 patent is incorporated herein by reference.

The product mixture of a reaction rarely is a single compound pure enough to comply with pharmaceutical standards. Side products and byproducts of the reaction and adjunct reagents used in the reaction will, in most cases, be present. At certain stages during processing of the rosuvastatin contained in the product mixture into an active pharmaceutical ingredient ("API"), the rosuvastatin must be analyzed for purity, typically by HPLC or GC analysis, to determine if it is suitable for continued processing or ultimately for use in a pharmaceutical product. The rosuvastatin does not need to be absolutely pure. Absolute purity is a theoretical ideal that is unattainable. Rather, there are purity standards intended to ensure that an API is not made less safe for clinical use because of the presence of impurities. In the United States, the Food and Drug Administration guidelines recommend that applicants limit some impurities to below 0.1%.

Generally, side products, byproducts and adjunct reagents (collectively "impurities") are identified spectroscopically and by other physical methods and then the impurities are associated with a peak position in a chromatogram (or a spot on a TLC plate). (Strobel p. 953) (Strobel, H. A.; Heineman, W. R., *Chemical Instrumentation: A Systematic Approach*, 3$^{rd}$ dd. (Wiley & Sons: New York 1989)). Thereafter, the impurity can be identified by its position in the chromatogram, which is conventionally measured in minutes between injection of the sample on the column and elution of the particular component through the detector, known as the "retention time." This time period varies daily based upon the condition of the instrumentation and many other factors. To mitigate the effect that such variations have upon accurate identification of an impurity, practitioners use "relative retention time" ("RRT") to identify impurities. (Strobel p. 922). The RRT of an impurity is its retention time divided by the retention time of some reference marker. In theory, rosuvastatin itself could be used as the reference marker, but as a practical matter it is present in such overwhelming proportion in the mixture that it tends to saturate the column, leading to irreproducible retention times, i.e., the maximum of the peak corresponding to rosuvastatin tends to wander (Strobel FIG. 24.8(b) p. 879, contains an illustration of the sort of asymmetric peak that is observed when a column is overloaded). Thus, it is sometimes desirable to select an alternative compound that is added to, or is present in, the mixture in an amount significant enough to be detectable and sufficiently low as not to saturate the column and to use that compound as the reference marker.

A compound in a relatively pure state can be used as a "reference standard" (a "reference marker" is similar to a reference standard but it is used for qualitative analysis) to quantify the amount of the compound in an unknown mixture. When the compound is used as an "external standard," a solution of a known concentration of the compound is analyzed by the same technique as the unknown mixture. (Strobel p. 924, Snyder p. 549) (Snyder, L. R.; Kirkland, J. J. *Introduction to Modern Liquid Chromatography*, 2nd ed. (John Wiley & Sons: New York 1979)). The amount of the compound in the mixture can be determined by comparing the magnitude of the detector response. See also U.S. Pat. No. 6,333,198, incorporated herein by reference.

The reference standard compound also can be used to quantify the amount of another compound in the mixture if the "response factor," which compensates for differences in the sensitivity of the detector to the two compounds, has been predetermined. (Strobel p. 894). For this purpose, the reference standard compound may be added directly to the mixture, in which case it is called an "internal standard." (Strobel p. 925, Snyder p. 552).

The reference standard compound can even be used as an internal standard when the unknown mixture contains some of the reference standard compound by using a technique called "standard addition," wherein at least two samples are prepared by adding known and differing amounts of the internal standard. (Strobel pp. 391-393, Snyder pp. 571, 572). The proportion of detector response due to the reference standard compound that is originally in the mixture can be determined by extrapolation of a plot of detector response versus the amount of the reference standard compound that was added to each of the samples to zero. (e.g. Strobel, FIG. 11.4 p. 392).

The present invention provides compounds that can be used as a reference standard and reference marker for quantification and identification of rosuvastatin and impurities present in batches of rosuvastatin.

A step in the synthesis of statins is reduction of a ketoester to yield the statin. For example, with fluvastatin, in U.S. Pat. No. 5,354,772, a ketoester of fluvastatin is reduced with EtB$_3$/NaBH$_4$ to obtain a diol ester. In another patent, U.S. Pat. No. 5,189,164 (EP 0 363 934), a ketoester of fluvastatin is reduced with diethylmethoxyborane to provide fluvastatin. Both these US patents relate to a process of purifying the FLV-diol ester by chromatography only. In U.S. Pat. No. 5,260,440, relating to rosuvastatin and in the U.S. Pat. No. 5,856,336, relating to pitavastatin, the statin-diol esters are also isolated by chromatography. In example 8 of WO 03/004455, 6-dibenzylcarbamoyl-5-hydroxy-3-oxo-hexanoic acid tert-butyl ester is reduced by hydrogenation at a pressure of 25 bar, followed by drying of ethyl acetate to obtain a residue having a syn to anti ratio of 7.6 to 1.

Reduction of a ketoester is also disclosed in Tetrahedron 49, 1997-2010 (1993). In the paper, reduction of a ketoester, which is not a particular statin, is carried out by EtB$_3$/NaBH$_4$ or RU-binap to provide a diol ester. In another paper, a ketoester, which is also not any particular statin, is reduced by catecholborane in the optional presence of Rh(PPh$_3$)Cl. JOC 55, 5190-5192 (1990).

The choice of reducing agents is an important factor in obtaining a statin from its corresponding ketoester since it influences the ratio of syn to anti obtained. The United States Pharmacopeia (USP) provides standards regarding the ratio of syn to anti that is used in a statin formulation. The USP requirements dictate use of a reducing agent that allows obtaining a high syn to anti ratio.

There is a need in the art for reducing agents which may be employed on an industrial scale on a cost effective basis, and which provide a high ratio of syn to anti and overall yield.

The diol ester obtained after reduction is usually not isolated, and is hydrolyzed to obtain a salt. For example, in U.S. Pat. No. 5,003,080, the intermediate ester isn't isolated at all. In one instance however, in Journal of Labeled Compounds & Radiopharmaceuticals vol. XLI, pages 1-7 (1988), a fluvastatin diol ester is obtained from hexane containing 3% isopropanol by volume. (See also TETRAHEDRON, VOL. 53 (31), 10659-10670, 1997)

We have yet found additional ways to increase the Syn to anti ratio of statins through isolation of the diol ester.

SUMMARY OF THE INVENTION

In one embodiment, the present invention provides a rosuvastatin triol having the following structure:

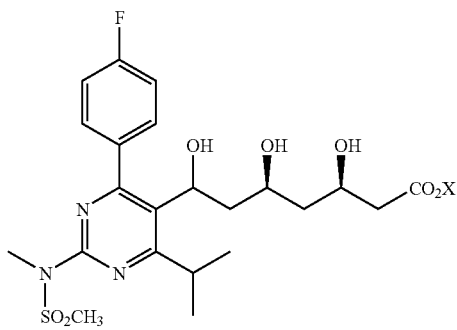

Wherein X is a hydrogen, a C$_1$-C$_4$ alkyl group, or an alkali or alkaline earth metal cation, with the proviso that when X is an alkaline earth metal, two molecules of rosuvastatin are present to one of the metal cation.

In another embodiment, the present invention provides a rosuvastatin triol in acid form has the following structure:

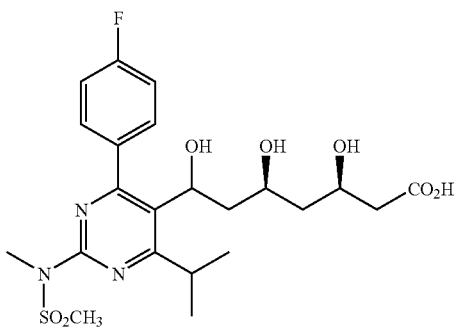

In yet another embodiment, the present invention provides a rosuvastatin triol in ester form having the following structure:

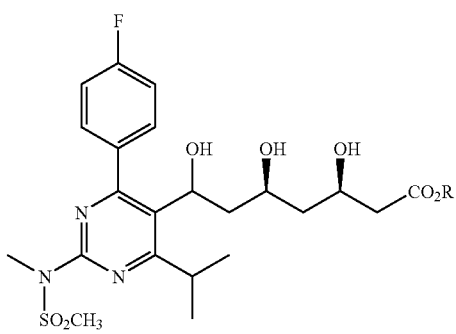

Wherein R is a $C_1$-$C_4$ alkyl ester.

In one embodiment, the present invention provides a rosuvastatin triol in salt form having the following structure:

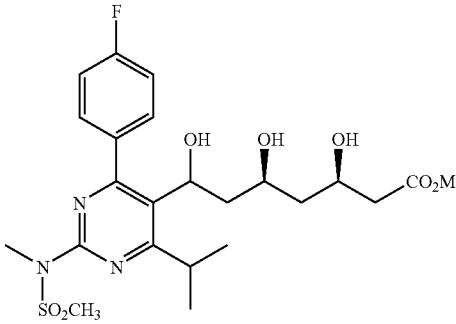

Wherein M is an alkali or alkaline earth metal cation, with the proviso that when X is an alkaline earth metal, two molecules of rosuvastatin are present to one of the metal cation.

In one embodiment, the present invention provides a rosuvastatin triol in lactone form having the following structure:

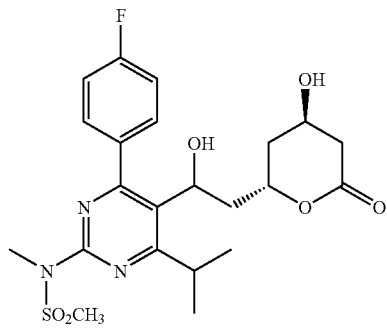

In another embodiment the present invention provides each of the above forms of the triol in isolated or purified form, substantially free of the corresponding rosuvastatin diol form.

In yet another embodiment, the present invention provides a process for preparing a rosuvastatin triol $C_1$-$C_4$ ester comprising combining rosuvastatin $C_1$-$C_4$ ester with a solution of borane dimethylsulfide complex in a suitable organic solvent to obtain a reaction mixture, combining the resulting reaction mixture with a solution of NaOH in water, adding hydrogen peroxide ($H_2O_2$) and recovering the triol ester.

In another embodiment the present invention provides a process for preparing rosuvastatin triol $C_1$-$C_4$ ester comprising oxidizing rosuvastatin diol $C_1$ to $C_4$ ester to obtain the rosuvastatin triol ester with a hydroxyl group at position 7.

In another embodiment the present invention provides a process comprising combining rosuvastatin $C_1$-$C_4$ ester with a solution of a borane in an organic solvent to obtain a reaction mixture, combining the resulting reaction mixture with a solution of an inorganic base in water, and adding peroxide and recovering the triol ester.

In one embodiment the present invention provides a process for reducing amount of impurities present in rosuvastatin calcium by measuring amount of rosuvastatin calcium triol in batches of rosuvastatin calcium, selecting batches of the rosuvastatin calcium with desirable level of the triol and preparing pharmaceutical compositions with the selected rosuvastatin calcium batch.

In another embodiment, the present invention provides a process for reducing amount of rosuvastatin triol calcium present in a mixture comprising rosuvastatin diol calcium and rosuvastatin triol calcium comprising measuring amount of rosuvastatin triol $C_1$-$C_4$ ester in batches of rosuvastatin diol $C_1$-$C_4$ ester, selecting batches of the rosuvastatin diol $C_1$-$C_4$ ester with of the triol $C_1$-$C_4$ ester and preparing pharmaceutical compositions of rosuvastatin diol calcium with the selected rosuvastatin diol $C_1$-$C_4$ ester batch.

In another embodiment, the present invention provides a method of determining the amount of an impurity in a sample of rosuvastatin ester (preferable t-butyl) comprising measuring by GC or HPLC the area under a peak corresponding to rosuvastatin triol ester in a reference standard comprising a known amount of rosuvastatin triol ester (preferably t-butyl); measuring by GC or HPLC the area under a peak corresponding to rosuvastatin triol ester in a sample comprising rosuvastatin triol and rosuvastatin diol esters (preferably t-butyl); and determining the amount of the rosuvastatin triol ester in the sample by comparing the area of reference standard with that of the test sample.

In yet another embodiment, the present invention provides a method of determining the amount of an impurity in a sample of rosuvastatin calcium comprising measuring by GC or HPLC the area under a peak corresponding to rosuvastatin triol calcium in a reference standard comprising a known amount of rosuvastatin triol calcium; measuring by GC or HPLC the area under a peak corresponding to rosuvastatin triol calcium in a sample comprising rosuvastatin triol and rosuvastatin diol calcium salts; and determining the amount of the triol calcium in the sample by comparing the area of reference standard with that of the test sample.

In one embodiment, the present invention provides a method of identifying the relative retention time (RRT) of an impurity in a sample of rosuvastatin diol ester (preferably t-butyl) comprising measuring by GC or HPLC the relative retention time (RRT) corresponding to rosuvastatin triol ester in a reference marker sample; carrying out GC or HPLC with a test sample comprising of the rosuvastatin diol ester and rosuvastatin triol ester to obtain an GC or HPLC chromatogram with retention times; and determining the relative retention time (RRT) of the triol ester in the sample by comparing the relative retention time (RRT) of the reference marker to the relative retention time (RRT) of the test sample.

In another embodiment, the present invention provides a method of identifying the relative retention time (RRT) of an impurity in a sample of rosuvastatin diol calcium comprising measuring by GC or HPLC the relative retention time (RRT) corresponding to rosuvastatin triol calcium in a reference marker sample; carrying out GC or HPLC with a test sample comprising of the rosuvastatin diol and rosuvastatin triol calcium salts to obtain an GC or HPLC chromatogram with retention times; and determining the relative retention time (RRT) of the triol calcium in the sample by comparing the relative retention time (RRT) of the reference marker to the relative retention time (RRT) of the test sample.

In one embodiment the present invention provides a process for preparing rosuvastatin triol acid with the following structure:

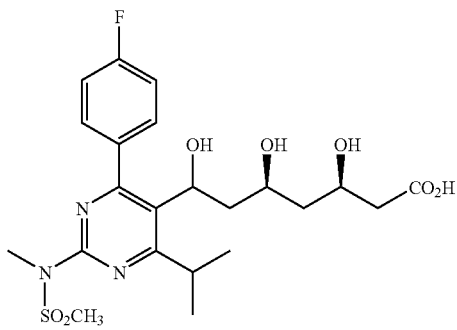

comprising hydrolyzing an ester of the following structure

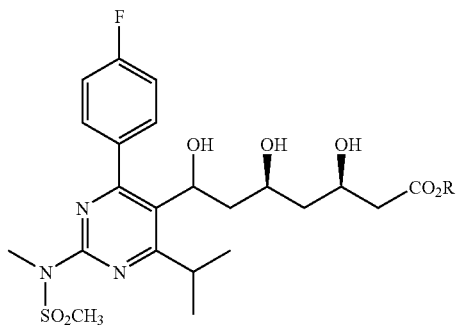

and converting the hydrolyzed ester with an acid, wherein R is a $C_1$-$C_4$ group.

In one embodiment the present invention provides a process for preparing rosuvastatin triol lactone with the following structure:

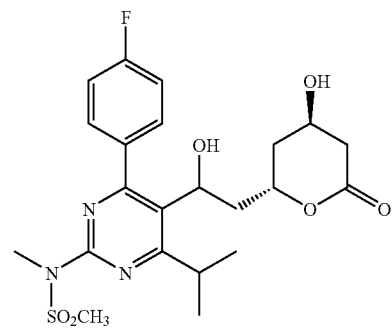

comprising hydrolyzing an ester of the following structure

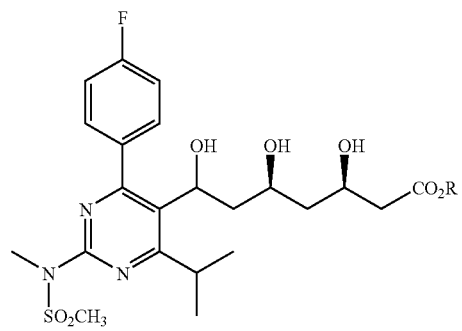

and converting the hydrolyzed ester to a lactone, wherein R is a $C_1$-$C_4$ ester.

In one embodiment the present invention provides a process for preparing rosuvastatin triol acid with the following structure:

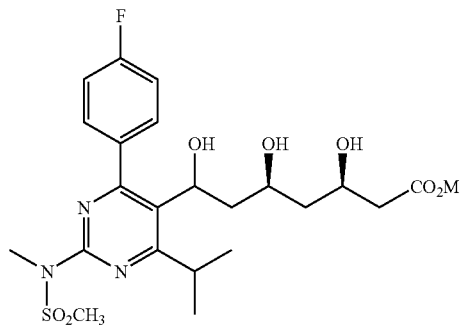

comprising hydrolyzing a lactone having the following structure

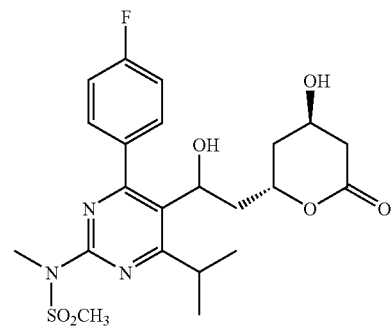

and converting the hydrolyzed lactone to an the salt, wherein M is an alkali metal or an alkaline earth metal with the proviso that if the metal cation is an alkaline earth metal, two molecules of rosuvastatin are present for each cation.

In one embodiment the present invention provides a process for preparing rosuvastatin triol salt with the following structure:

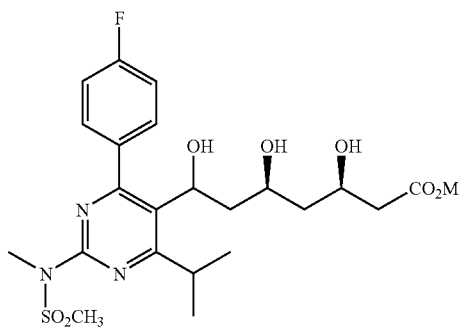

Comprising contacting an acid with the following structure

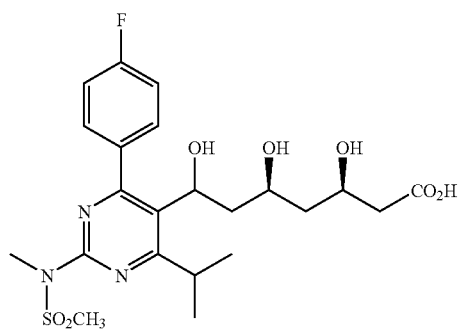

with a base, with the proviso that if the metal cation is an alkaline earth metal, two molecules of rosuvastatin are present for each cation.

In one embodiment, the present invention provides a process for preparing rosuvastatin diol ester comprising the steps of
a) combining B-Methoxy-9-BBN, an organic and a ketoester having the formula:

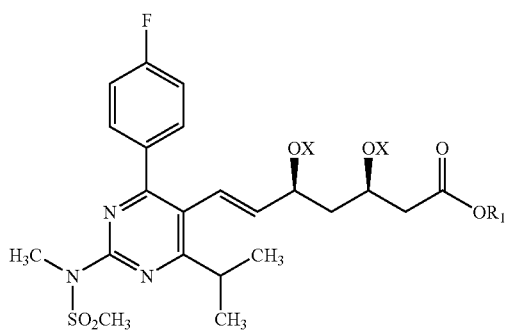

wherein $R_1$ is a straight or branched $C_1$ to $C_4$ alkyl group, and wherein at least one X forms a double bond to give a ketone, and at most one X is a hydrogen, to obtain a reaction mixture,
b) combining a source of hydride ions with the reaction mixture, and
c) maintaining the reaction mixture to obtain the rosuvastatin diol ester.

In another embodiment, the present invention provides a process for preparing rosuvastatin from a rosuvastatin diol-ester having the formula:

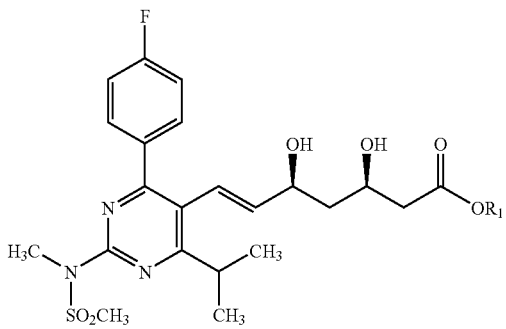

wherein $R_1$ is a straight or branched $C_1$ to $C_4$ alkyl group; comprising the steps of
a) combining a ketoester of rosuvastatin having the formula:

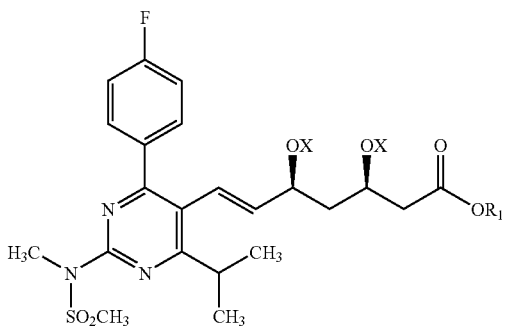

with a solvent to form a solution, wherein $R_1$ is a straight or branched $C_1$ to $C_4$ alkyl group, and wherein at least one X forms a double bond to give a ketone, and at most one X is a hydrogen;
b) cooling the solution to a temperature of about −50° C. to about −80° C.;
c) combining B-Methoxy-9-BBN with the solution to obtain a reaction mixture, and maintaining the reaction mixture for at least about 30 minutes;
d) combining a source of hydride ions with the reaction mixture, and maintaining the reaction mixture for an additional period of at least about 2 hours;
e) quenching the reaction mixture;
f) recovering the rosuvastatin diol-ester; and
g) converting the rosuvastatin diol-ester to rosuvastatin or a pharmaceutically acceptable salt of rosuvastatin.

In another embodiment, the present invention provides a process for preparing rosuvastatin from a rosuvastatin ketoester having the formula:

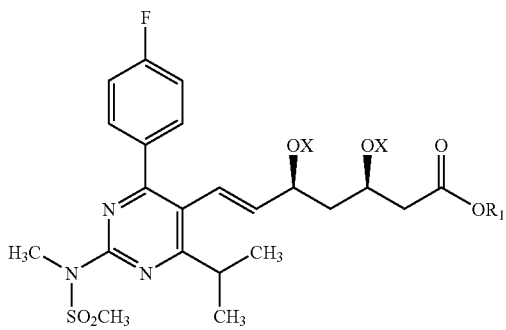

wherein $R_1$ is a straight or branched $C_1$ to $C_4$ alkyl group, and wherein at least one X forms a double bond to give a ketone, and at most one X is a hydrogen, comprising the steps of a) combining the ketoester of rosuvastatin with a solvent to form a solution;

b) cooling the solution to a temperature of about −50° C. to about −80° C.;

c) combining B-Methoxy-9-BBN with the solution to obtain a reaction mixture and maintaining the reaction mixture for at least about 30 minutes;

d) combining a source of the hydride ions to the reaction mixture and maintaining the reaction mixture for an additional period of at least about 2 hours to obtain rosuvastatin diol ester;

e) quenching the reaction mixture;

f) combining the rosuvastatin diol ester with NaOH or $Ca(OH)_2$ and a solvent or a mixture of solvent and water; and g) recovering the rosuvastatin free acid, lactone or a pharmaceutically acceptable salt thereof.

DETAILED DESCRIPTION OF THE INVENTION

Figure 1:
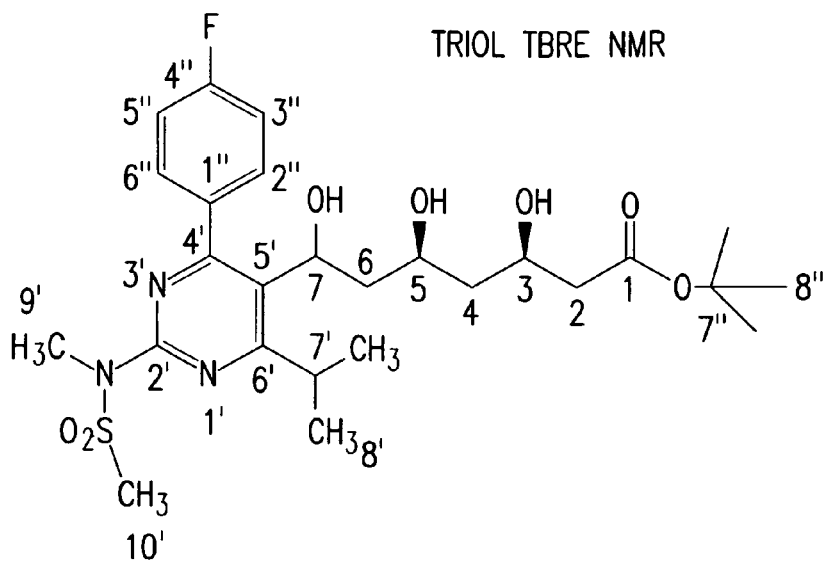
FIG. 1 is an NMR of TBRE (t-butyl Rosuvastatin Ester) triol.

As used herein, the term "diol" refers to the two hydroxyl groups present on rosuvastatin. Diol rosuvastatin is used herein synonymously as rosuvastatin.

As used herein the term "substantially free" refers to having less than about 30% of the corresponding compound (e.g., diol or diastereoisomer), more preferably less than about 20%, even more preferably less than about 10%, and most preferably less than about 5%, based on area percentage HPLC.

As used herein, the term "triol lactone" refers to the lactone of rosuvastatin triol.

As used herein, the term "reference standard" refers to a compound that may be used both for quantitative and qualitative analysis of an active pharmaceutical ingredient. For example, the retention time of the compound in HPLC allows for setting a relative retention time, thus making qualitative analysis possible. The concentration of the compound in solution before injection into an HPLC column allows for comparison of the areas under the peaks in an HPLC chromatogram, thus making quantitative analysis possible.

A "reference marker" is used in qualitative analysis to identify components of a mixture based upon their position, e.g. in a chromatogram or on a Thin Layer Chromatography (TLC) plate (Strobel pp. 921, 922, 953). For this purpose, the compound does not necessarily have to be added to the mixture if it is present in the mixture. A "reference marker" is used only for qualitative analysis, while a reference standard may be used for quantitative or qualitative analysis, or both. Hence, a reference marker is a subset of a reference standard, and is included within the definition of a reference standard.

Although some of the knowledge of those in the art regarding reference standards has been described in general terms up to this point, those skilled in the art also understand that the detector response can be, for example, the peak heights or integrated peak areas of a chromatogram obtained, e.g. by UV or refractive index detection, from the eluent of an HPLC system or, e.g. flame ionization detection or thermal conductivity detection, from the eluent of a gas chromatograph, or other detector response, e.g. the UV absorbance, of spots on a fluorescent TLC plate. The position of the reference standard may be used to calculate the relative retention time for rosuvastatin and other impurities.

The present invention provides a rosuvastatin triol having the following structure:

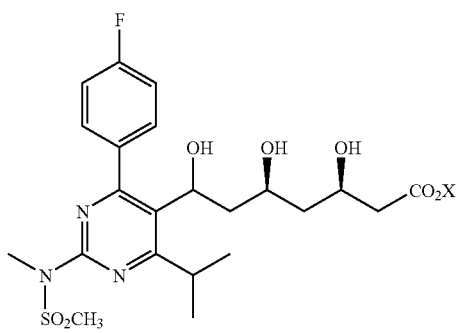

wherein X is a hydrogen, an alkali or alkaline earth metal or a $C_1$-$C_4$ alkyl group. Preferably X is hydrogen (i.e. rosuvastatin triol acid), calcium ($Ca^{2+}$) (i.e. rosuvastatin triol calcium) or tert-butyl (i.e. rosuvastatin triol tert-butyl ester ("TBRE")).

The present invention provides a rosuvastatin triol having the following structure:

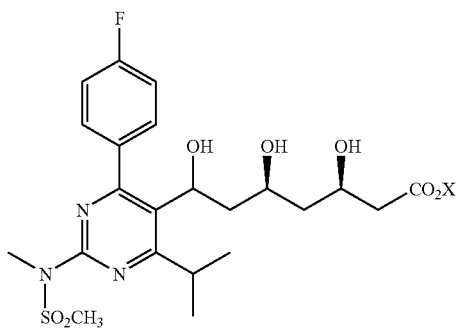

wherein X is a hydrogen, an alkali or alkaline earth metal or a $C_1$-$C_4$ alkyl group. Preferably X is hydrogen (i.e. rosuvastatin triol acid), calcium ($Ca^{2+}$) (i.e. rosuvastatin triol calcium) or tert-butyl (i.e. rosuvastatin triol tert-butyl ester ("TBRE")) in its isolated form.

The present invention provides a rosuvastatin triol in an acid form having the following structure:

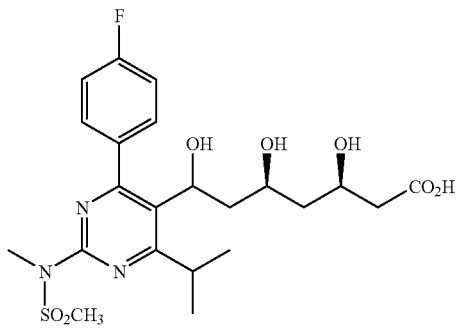

The present invention provides rosuvastatin triol in ester form having the following structure

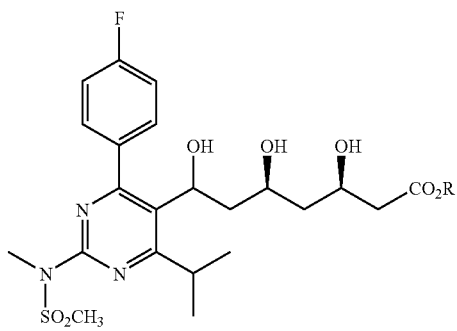

wherein R is a $C_1$-$C_4$ alkyl group. Preferably, R is a t-butyl or methyl group. More preferably, the R is t-butyl.

The present invention provides rosuvastatin triol in a salt form having the following structure:

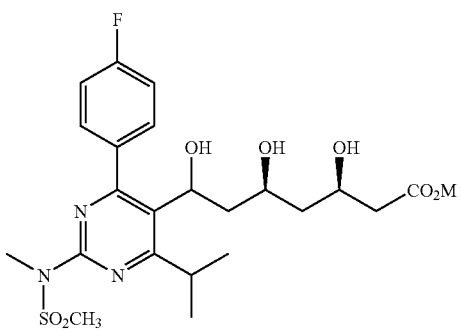

wherein M is an alkali metal or alkaline earth metal cation. Preferably, M is calcium. One of ordinary skill of art would appreciate that when M is an alkaline earth metal cation, such as calcium, the salt would be a hemi calcium salt (2:1 ratio):

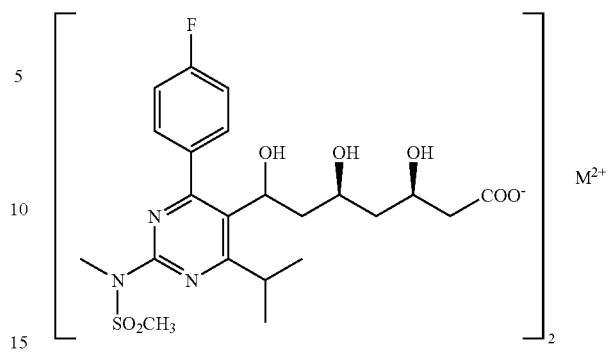

The present invention further provides rosuvastatin triol in lactone form has the following structure:

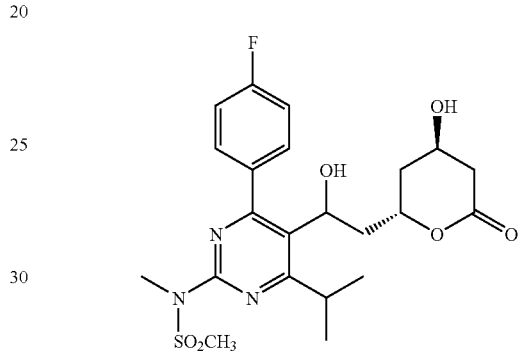

The present invention also provides each of the above forms of the rosuvastatin triol substantially free of the corresponding rosuvastatin diol form. Thus, the present invention provides:

a) Rosuvastatin triol $C_1$-$C_4$ ester substantially free of rosuvastatin diol $C_1$-$C_4$ ester. Also provided is rosuvastatin triol t-butyl ester substantially free of rosuvastatin diol t-butyl ester;

b) Rosuvastatin triol acid substantially free of rosuvastatin diol acid;

c) Rosuvastatin triol salt (preferably calcium salt) substantially free of rosuvastatin diol salt (preferably calcium salt); and d) Rosuvastatin triol lactone substantially free of rosuvastatin diol lactone.

The present invention also provides each of the above forms of the rosuvastatin triol in racemic, (7S) and (7R) configuration. The (7S) and (7R) configurations are diastereoisomers.

Specifically, the present invention provides:

a) Rosuvastatin triol $C_1$-$C_4$ ester, preferably t-butyl ester, in racemic, (7S) and (7R) forms. In one embodiment, the (7S) form is substantially free of the (7R) form. In one embodiment, the (7R) form is substantially free of the (7S) form.

b) Rosuvastatin triol acid in racemic, (7S) and (7R) forms. In one embodiment, the (7S) form is substantially free of the (7R) form. In one embodiment the (7R) form is substantially free of the (7S) form.

c) Rosuvastatin triol salt (such as calcium), in racemic, (7S) and (7R) forms. In one embodiment, the (7S) form is substantially free of the (7R) form. In one embodiment the (7R) form is substantially free of the (7S) form.

d) Rosuvastatin triol lactone in racemic, (7S) and (7R) forms. In one embodiment, the (7S) form is substantially free of the (7R) form. In one embodiment, the (7R) form is substantially free of the (7S) form.

The present invention also provides a method for preparing rosuvastatin triol ester. The triol ester can be prepared by oxidizing rosuvastatin $C_1$-$C_4$ ester, particularly t-butyl ester. The oxidation of the ester can be carried out by combining rosuvastatin $C_1$-$C_4$ ester, particularly t-butyl ester, with borane (e.g. $BH_3$, $B_2H_6$). Complexes of borane, as well as various monoalkyl ($C_1$-$C_8$)- and dialkyl ($C_1$-$C_8$)-boranes may be used. Preferably, a solution of borane dimethylsulfide complex in a suitable organic solvent is combined with the ester. The reaction mixture can be stirred. A solution of an inorganic base, preferably NaOH, in water is then combined with the reaction mixture followed by addition of $H_2O_2$ (preferably about 30% in water). The $H_2O_2$ is preferably added dropwise. The temperature during $H_2O_2$ addition is preferably kept below about 50° C.

In addition to $H_2O_2$, other oxidation reagents can be used. For example, any other peroxides can be used including t-Butyl Hydroperoxide (TBHP) and Magnesium monoperoxyphthalate hexahydrate (MMPP).

The inorganic base is preferably an alkali metal base, more preferably a hydroxide base, such as NaOH, KOH and LiOH. Another base that can be used is $NH_4OH$.

The organic phase can be separated and washed with water and/or brine to remove water miscible by-products such as borane by products (e.g.: $H_3BO_3$). It can also be washed with sodium sulphite to remove excess hydrogen peroxide. The organic phase can then be concentrated to obtain a residue. Concentration can be done by reducing the pressure to less than 1 atmosphere such as less than about 100 mmHg.

After the reaction, if desired, a precipitating agent, such as ammonium chloride or another salt can be added to precipitate impurities out of the reaction mixture. Ammonium chloride is used to remove $H_3BO_3$, the reaction-by-product. Instead of using ammonium chloride, an acid such as acetic acid or HCl can be used to neutralize the basic mixture. The $H_3BO_3$ can be removed by washing with water.

The rosuvastatin triol ester can then be purified and isolated from the corresponding rosuvastatin diol ester by chromatography.

The present invention provides rosuvastatin triol ester in its isolated form.

The triol ester can then be converted to the corresponding acid, salt or lactone.

The triol ester can be converted to the triol salt by hydrolysis of the ester and addition of a suitable source of ions. To obtain the calcium salt either a combination of sodium hydroxide and calcium chloride can be used, or calcium hydroxide can be used.

The rosuvastatin ester can be converted to the salt by suspending the ester in a mixture of an organic solvent and water mixture and combined with a base such as sodium hydroxide to obtain a solution. The organic solvent may be $C_1$-$C_4$ alcohol, preferably ethanol. The organic solvent is then evaporated under reduced pressure followed by addition of calcium chloride, which results in precipitation of the calcium salt of the triol. The precipitate can be recovered by conventional techniques such as filtration.

The present invention provides rosuvastatin triol salt in its isolated form.

To obtain the rosuvastatin triol acid, the salt is combined with an acid, such as hydrochloric or sulfuric acid. In one embodiment Rosuvastatin triol calcium is suspended in an organic solvent such as dichloromethane, to which aqueous HCl is added. The rosuvastatin triol acid is then isolated from the reaction mixture, such as by separation of the organic phase followed by removal of organic solvent, such as by evaporation under reduced pressure.

The acid can also be obtained after hydrolysis of the ester, by acidification of the reaction mixture instead of addition of calcium chloride. Inorganic acids such as HCl and $H_2SO_4$ can be used.

The present invention provides rosuvastatin triol acid in its isolated form.

The rosuvastatin lactone can then be obtained from the acid under conditions that favor lactonization. In one embodiment, rosuvastatin triol calcium is dissolved in in an organic solvent such as acetonitrile, to which aqueous HCl is added. The reaction mixture can then be stirred. The organic solvent and water can then be removed, such as by evaporation under reduced pressure to obtain the lactone.

Figure 2:
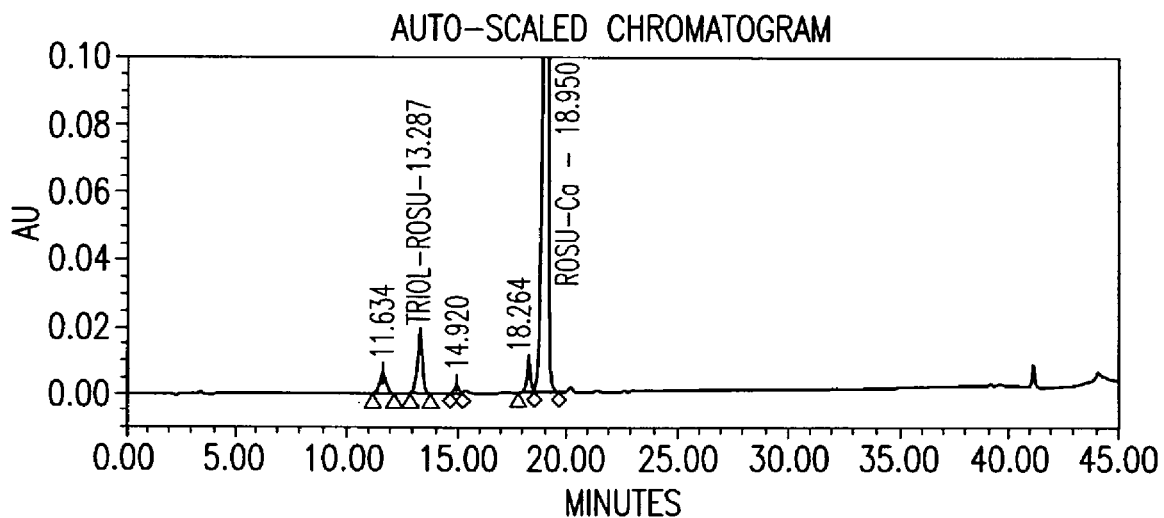
FIG. 2 is an HPLC chromatogram illustrating use of rosuvastatin triol calcium as a reference standard (including a reference marker).

As stated above, these compounds, namely rosuvastatin triol acid, salt, lactone and ester can be used as reference marker/standards. FIG. 2 illustrates that the compounds of the present invention can used as reference standards to both quantify and identify amount of impurities present in a composition of rosuvastatin. Rosuvastatin triol calcium is close to rosuvastatin diol calcium on the column, yet does not overlap with the peak for rosuvastatin. This lack of overlap is ideal since it can make quantification easier.

The present invention provides rosuvastatin triol lactone in its isolated form.

The present invention provides a process for reducing amount of rosuvastatin triol calcium present in a mixture comprising rosuvastatin calcium and rosuvastatin triol calcium comprising measuring amount of rosuvastatin calcium triol in batches of rosuvastatin diol calcium, selecting batches of the rosuvastatin diol with desirable level of the triol and preparing pharmaceutical compositions with the selected rosuvastatin diol batch. Salts in general other than calcium can also be used in this process.

The present invention provides a process for reducing amount of rosuvastatin triol calcium present in a mixture comprising rosuvastatin diol calcium and rosuvastatin triol calcium comprising measuring amount of rosuvastatin triol $C_1$-$C_4$ ester in batches of rosuvastatin diol $C_1$-$C_4$ ester, selecting batches of the rosuvastatin diol $C_1$-$C_4$ ester with of the triol $C_1$-$C_4$ ester and preparing pharmaceutical compositions of rosuvastatin diol calcium with the selected rosuvastatin diol $C_1$-$C_4$ ester batch. The ester is preferably t-butyl.

The present invention provides a process for reducing amount of rosuvastatin triol calcium present in a mixture comprising rosuvastatin diol calcium and rosuvastatin triol calcium comprising measuring amount of rosuvastatin triol lactone in batches of rosuvastatin diol lactone, selecting batches of the rosuvastatin diol lactone with desirable level of the triol lactone and preparing pharmaceutical compositions of rosuvastatin diol calcium with the selected rosuvastatin diol lactone batch.

The present invention provides a process for reducing amount of rosuvastatin triol calcium present in a mixture comprising rosuvastatin diol calcium and rosuvastatin triol calcium comprising measuring amount of rosuvastatin triol acid in batches of rosuvastatin diol acid, selecting batches of the rosuvastatin diol acid with desirable level of the triol acid and preparing pharmaceutical compositions of rosuvastatin diol calcium with the selected rosuvastatin diol acid batch.

The present invention provides a method of determining the amount of an impurity in a sample of rosuvastatin diol ester (preferable t-butyl ester) comprising measuring by GC or HPLC the area under a peak corresponding to rosuvastatin triol ester in a reference standard comprising a known amount of rosuvastatin triol ester (preferably t-butyl); measuring by GC or HPLC the area under a peak corresponding to rosuvastatin triol ester in a test sample comprising rosuvastatin triol and rosuvastatin diol esters (preferably t-butyl); and determining the amount of the triol ester in the sample by comparing the area of reference standard with that of the test sample.

The present invention provides a method of determining the amount of an impurity in a sample of rosuvastatin calcium comprising measuring by GC or HPLC the area under a peak corresponding to rosuvastatin triol calcium in a reference standard comprising a known amount of rosuvastatin triol calcium; measuring by GC or HPLC the area under a peak corresponding to rosuvastatin triol calcium in a test sample comprising rosuvastatin triol and rosuvastatin diol calcium salts; and determining the amount of the triol calcium in the sample by comparing the area of reference standard with that of the test sample. Salts in general other than calcium can also be used in this process.

The present invention provides a method of determining the amount of an impurity in a sample of rosuvastatin acid comprising measuring by GC or HPLC the area under a peak corresponding to rosuvastatin triol acid in a reference standard comprising a known amount of rosuvastatin triol acid; measuring by GC or HPLC the area under a peak corresponding to rosuvastatin triol acid in a test sample comprising rosuvastatin acid and rosuvastatin diol acid; and determining the amount of the triol acid in the sample by comparing the area of reference standard with that of the test sample.

The present invention provides a method of determining the amount of an impurity in a sample of rosuvastatin lactone comprising measuring by GC or HPLC the area under a peak corresponding to rosuvastatin triol lactone in a reference standard comprising a known amount of rosuvastatin triol lactone; measuring by GC or HPLC the area under a peak corresponding to rosuvastatin triol lactone in test a sample comprising rosuvastatin triol lactone and rosuvastatin diol lactone; and determining the amount of the triol lactone in the sample by comparing the area of reference standard with that of the test sample.

The present invention provides a method of identifying the relative retention time (RRT) of an impurity in a sample of rosuvastatin diol ester (preferably t-butyl) comprising measuring by GC or HPLC the relative retention time (RRT) corresponding to rosuvastatin triol ester in a reference marker sample; carrying out GC or HPLC with a test sample comprising of the rosuvastatin ester and rosuvastatin triol ester to obtain an HPLC or GC chromatogram with retention times; and determining the relative retention time (RRT) of the triol ester in the sample by comparing the relative retention time (RRT) of the reference marker to the relative retention time (RRT) of the test sample. Preferably the rosuvastatin diol and rosuvastatin triol ester are tert-butyl esters.

Accordingly in another embodiment, the present invention provides a method of determining the relative retention time (RRT) of an impurity in a sample of rosuvastatin diol calcium comprising measuring by GC or HPLC the relative retention time (RRT) corresponding to rosuvastatin triol calcium in a reference marker sample; carrying out GC or HPLC with a test sample comprising of the rosuvastatin diol and rosuvastatin triol calcium salts to obtain an HPLC chromatogram with retention times; and determining the relative retention time (RRT) of the triol calcium in the sample by comparing the relative retention time (RRT) of the reference marker to the relative retention time (RRT) of the test sample. Salts in general other than calcium can also be used in this process.

Accordingly in another embodiment, the present invention provides a method of identifying the relative retention time (RRT) of an impurity in a sample of rosuvastatin diol acid comprising measuring by GC or HPLC the relative retention time (RRT) corresponding to rosuvastatin triol acid in a reference marker sample; carrying out GC or HPLC with a test sample comprising of the rosuvastatin diol acid and rosuvastatin triol acid to obtain an HPLC chromatogram with retention times; and determining the relative retention time (RRT) of the triol acid in the sample by comparing the relative retention time (RRT) of the reference marker to the relative retention time (RRT) of the test sample.

Accordingly in another embodiment, the present invention provides a method of determining the relative retention time (RRT) of an impurity in a sample of rosuvastatin diol lactone comprising measuring by GC or HPLC the relative retention time (RRT) corresponding to rosuvastatin triol lactone in a reference marker sample; carrying out GC or HPLC with a test sample comprising of the rosuvastatin diol acid and rosuvastatin triol acid to obtain an HPLC chromatogram with retention times; and determining the relative retention time (RRT) of the triol acid in the sample by comparing the relative retention time (RRT) of the reference marker to the relative retention time (RRT) of the test sample.

The present invention provides methods for reduction of a statin ketoester by use of 9-methoxy-9-bora-bicyclo[3.3.1]nonane (B-methoxy-9-BBN) as a complexant agent. Complexation with B-methoxy-9-BBN (BM-9-BBN) provides ideal selectivity. The requirement for fluvastatin diol ester is no more than about 0.8% by area % HPLC of the anti product. The reduction process of the present invention yields, in case of fluvastatin, about 0.5 to 0.6% anti by area % HPLC, and other crystallization steps yield less than about 0.2% anti by area % HPLC. Additionally, B-methoxy-9-BBN may be used in a molar ratio as low as about 1:1.

The ketoester reduced in the present invention, which is exemplified by fluvastatin and rosuvastatin, has the following for

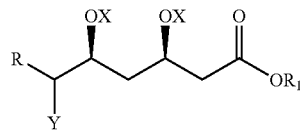

wherein $R_1$ is a $C_1$ to $C_4$ alkyl group (t-butyl preferred), R is an organic radical as described below, Y is a hydrogen or forms a double bond with the R group and at least one of the X's forms a double bond with the carbons being attached to the oxygen to give a ketone, and at most one X is hydrogen. A preferred reaction scheme is illustrated below, where the X closest to the ester forms a ketone and the other X is a hydrogen (alpha ketoester):

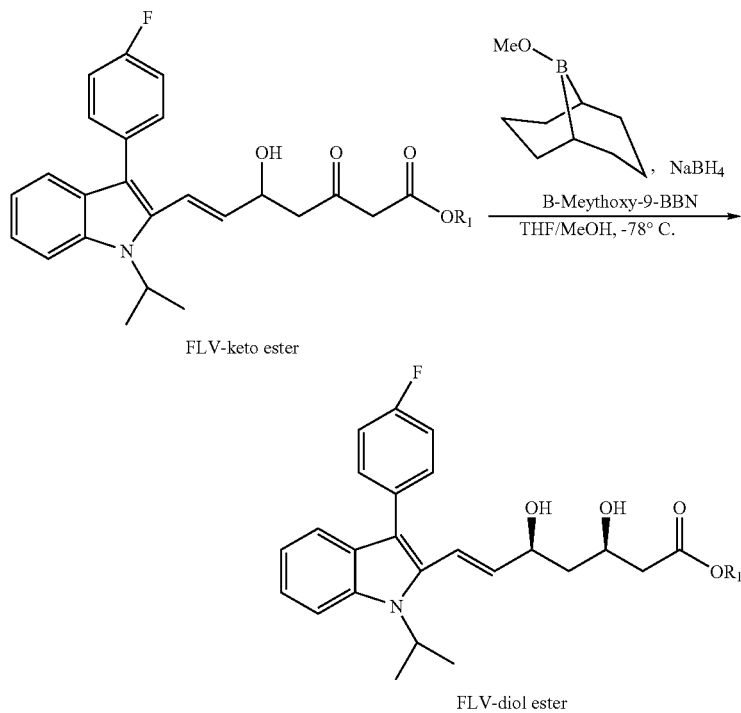

FLV-keto ester

FLV-diol ester

As used herein, $R_1$ refers to an organic radical that is bonded to the diol pentanoic ester group and is inert to reduction with the reducing agent and allows for therapeutic activity. By inert to reduction it is meant that the reducing agent employed does not reduce the R Group according to the general knowledge of one of skill in the art. Depending on the statin, the R radical can be:

pravastatin: 1,2,6,7,8,8a-Hexahydro-6-hydroxy-2-methyl-8-(2-methyl-1-oxobutoxy)-1-naphthalene ethyl radical.

fluvastatin: 3-(4-fluorophenyl)-1-(1-methylethyl)-1H-indol-2-yl]-ethylene radical.

cerivastatin: 4-(4-fluorophenyl)-5-methoxymethyl)-2,6-bis (1-methylethyl)-3-pyridinyl-ethylene radical.

atorvastatin: 2-(4-fluorophenyl)-5-(1-methylethyl)-3-phenyl-4-[(phenylamino)carbonyl]-1H-pyrrole-ethyl radical.

rosuvastatin: [4-(4-fluorophenyl)-6-(1-methylethyl)-2-[methyl(methylsulfonyl)amino]-5-pyrimidinyl]-ethylene radical.

pitavastatin: [4'-(4''-fluorophenyl)-2'-cyclopropyl-quinolin-3'-yl]-ethylene radical.

The R radical can also be that of the open ring form, i.e., the dihydroxy acid, of simvastatin or lovastatin. These open ring forms also have a diol pentanoic acid group. As used herein, the terms simvastatin and lovastatin include both the lactone form and the open-ring form, unless otherwise indicated by a formula. When the statin is simvastatin or lovastatin, the R radical is:

simvastatin: 1,2,6,7,8,8a-Hexahydro-2,6-dimethyl-8-(2,2-dimethyl-1-oxobutoxy)-1-naphthalene ethyl radical.

lovastatin: 1,2,6,7,8,8a-Hexahydro-2,6-dimethyl-1-8-(2-methyl-1-oxobutoxy)-1-naphthalene ethyl radical.

The reduction of the statin ketoester, with B-Methoxy-9-BBN includes combining the statin ketoester and a solvent; cooling the solution to a temperature of about −50° C. to about −80° C.; adding B-Methoxy-9-BBN and maintaining the reaction mixture for at least about 30 minutes; adding a source of hydride ions and maintaining the reaction mixture for an additional period of at least about 2 hours; adding a quenching agent; and recovering the statin diol-ester. The solvent may include $C_1$ to $C_4$ alcohols such as methanol, dipolar solvents such as tetrahydrofuran, $C_2$ to $C_8$ ethers cyclic or acyclic, or a mixture thereof. Preferably, the solution is cooled to about −70° C. to about −80° C. An optimum temperature is about −70° C., which allows for greater selectivity. The source of hydride ions may be sodium borohydride, potassium borohydride and lithium borohydride, preferably sodium borohydride. The quenching agent may be any one of hydrogen peroxide, sodium carbonate 1.5$H_2O$ or $NaBO_3.H_2O$, 3-chloroperbenzoic acid, ammonium chloride, aqueous solution of HCl, acetic acid, oxone, sodium hypochlorite, dimethyl disulfide, diethanolamine, hydroxylamine-O-sulfonic acid, acetone, preferably hydrogen peroxide. The quenching agent is used for terminating the reaction, by reacting it with the remaining reducing agent.

After quenching the reaction, the statin diol-ester may be recovered from the reaction mixture by adding a $C_4$ to $C_7$ ester and water, separating the organic phase from the two-phase system that formed, and removing the solvent by any technique known in the art (such as evaporation).

In one embodiment of the invention, the process of preparing a $C_1$ to $C_4$ alkyl ester of rosuvastatin, preferably t-butyl rosuvastatin ester (TBRE), includes adding a source of hydride ions to a solution of the rosuvastatin ester and MeO-9-BBN. This process includes forming a complex of the ketoester and MeO-9-BBN, followed by reduction with a source of hydride ions.

In a preferred embodiment, the process includes the steps of: providing a solution of rosuvastatin $C_1$-$C_4$ keto-ester and MeO-9-BBN in an organic solvent; adding a source of hydride ions to the solution; and maintaining the solution for a time sufficient to obtain the corresponding diol ester.

In one embodiment, the $C_1$-$C_4$ ester, including TBRE has diastereomeric impurities of 0.37%.

The solution of rosuvastatin keto-ester and MeO-9-BBN may be prepared by combining the rosuvastatin keto-ester and MeO-9-BBN with a suitable organic solvent. Preferably, a dilution of MeO-9-BBN of about 30 to about 60 volumes (vs. rosuvastatin keto-ester) is used in the process of the invention.

Suitable organic solvents include $C_1$ to $C_4$ alcohols, polar solvents, cyclic or acyclic $C_3$ to $C_8$ ethers, and mixtures of these. Specific examples of solvents include methylene chloride, toluene, methyl t-butyl ether, di-ethyl ether, tetrahydrofuran, dioxane, methanol, ethanol, isopropanol and n-butanol.

In one preferred embodiment, the reduction of rosuvastatin ketoester to rosuvastatin diol ester may be carried out in a mixture of methanol and THF. Other solvents as specified above may be used. The optimum temperature of the reduction is at a temperature below about −70° C., more preferably about −78° C. B-Methoxy-9-BBN is added to a solution of the ester at this optimal temperature, followed by addition of a suitable source of hydride ions. The source of hydride ions may be sodium borohydride, potassium borohydride and lithium borohydride, preferably sodium borohydride. Sodium borohydride is a preferred source of hydride ions in this embodiment of the invention.

The reaction may be quenched after its completion. Preferably, the quenching agent is selected from the group consisting of: hydrogen peroxide, 3-chloroperbenzoic acid, ammonium chloride, aqueous solution of HCl, acetic acid, oxone, sodium hypochlorite, dimethyl disulfide, diethanolamine, hydroxylamine-O-sulfonic acid and acetone. More preferably, the quenching agent is hydrogen peroxide. Rosuvastatin diol ester may be recovered from a biphasic mixture of water and a water immiscible organic solvent, where the ester moves into the organic phase. It may then be washed under basic and brine conditions. Preferred water immiscible organic solvents are ethyl acetate, toluene or methyl ethyl ketone, with ethyl acetate being most preferred.

According to USP pharmacopoeia, the level of anti-isomer should be NMT 0.8% (% area by HPLC according to USP HPLC method). In order to increase the syn to anti isomer ratio the statin diol-ester may be crystallized.

In one embodiment, fluvastatin diol-ester in the present invention may be crystallized from the following solvents: $C_3$ to $C_7$ ketone such as acetone, $C_1$ to $C_4$ alcohol such as ethanol, isopropyl alcohol, 1-propanol, 2-propanol 1-butanol and 2-butanol, $C_3$ to $C_7$ ester other than ethyl acetate such as isopropylacetate, isobutylacetate or methyl acetate, $C_1$-$C_4$ ethers other than MTBE (methyl t-butyl ether), and mixtures thereof. The crystallization solvent may also be a mixture of MTBE and $C_1$ to $C_4$ alcohols, preferably MTBE and IPA (iso-propanol). The crystallization includes the steps of: dissolving the statin diol-ester in said solvent at elevated temperature; cooling the solution; and recovering the crystallized fluvastatin diol ester. Preferably, the solvent is selected from the group consisting of: acetone, IPA, isopropylacetate, acetonitrile, mixtures thereof (with or without water) and a mixture of IPA/MTBE. The elevated temperature is preferably above about 30° C., more preferably above about 40° C. and most preferably about reflux temperature. The precipitate obtained may be recovered by conventional techniques such as filtration and concentration. Preferably, the fluvastatin is dissolved at reflux. Seeding may also be used for crystallization.

The fluvastatin diol-ester may also be crystallized by using a solvent and an anti-solvent. This comprises the steps of: dissolving the statin diol-ester in a $C_3$ to $C_7$ ketone solvent such as acetone, methylethylketone and methyl isopropyl ketone, at elevated temperature; adding a $C_5$ to $C_{12}$ saturated hydrocarbon such as cyclic and acyclic heptane and hexane; cooling the solution; and recovering the crystallized diol ester. Preferably, the cooling is at a temperature of from about 10° C. to about 25° C. Preferably, the elevated temperature is the reflux temperature. In one embodiment, a $C_1$ to $C_4$ alcohol is used with less than 50% hydrocarbon by volume, more preferably without a hydrocarbon.

The term "anti-solvent" refers to a liquid that, when added to a solution of fluvastatin diol ester in a solvent, induces precipitation of fluvastatin sodium. The anti-solvent may also be in a binary mixture with the solvent when the solution is prepared. Precipitation of fluvastatin diol ester is induced by the anti-solvent when addition of the anti-solvent causes fluvastatin diol ester to precipitate from the solution more rapidly or to a greater extent than fluvastatin diol ester precipitates from a solution containing an equal concentration of fluvastatin diol ester in the same solvent when the solution is maintained under the same conditions for the same period of time but without adding the anti-solvent. Precipitation can be perceived visually as a clouding of the solution or formation of distinct particles of fluvastatin diol ester suspended in or on the surface of the solution or collected on the walls or at the bottom of the vessel containing the solution.

The above crystallizations may allow for increasing the syn to anti ratio so that the level of the anti isomer is about 0.2 or less % area by HPLC. Preferably the level of the anti isomer is about 0.04 or less % area by HPLC.

In another embodiment, rosuvastatin diol ester is crystallized or slurried. Crystallization of the diol ester includes preparing a solution of the C1-C4 ester, including TBRE in a solvent selected from the group consisting of: $C_1$-$C_4$ alcohols, $C_3$-$C_8$ esters, $C_3$-$C_8$ ketones, $C_3$-$C_8$ ethers, $C_6$ to $C_{10}$ aromatic hydrocarbons, PGME (propylene glycol monomethyl ether), water, acetonitrile, and mixtures thereof; cooling the solution to crystallize the diol ester; and recovering the crystallized diol ester. Slurrying can be carried out in the same solvents, followed by recovery of the diol ester. Preferably, the recovery comprises filtering the slurry to obtain a precipitate. Preferably, the filtration is under reduced pressure. Preferably, the obtained precipitate is further dried.

Most preferably the solvent of crystallization is toluene or a mixture of methanol/water or acetonitrile/water.

The diol ester may be further converted into a pharmaceutically acceptable salt of the statin or a lactone. In one embodiment, the diol ester obtained is reacted with sodium or calcium hydroxide to obtain the sodium or calcium salt. It is also possible to first obtain the sodium salt by reaction with sodium hydroxide, and then convert the sodium salt to calcium salt by using a source of calcium such as calcium chloride or calcium acetate. The basic hydrolysis of the statin diol-ester may be carried out with one or more equivalents of an alkali metal or alkaline earth metal base such as NaOH or Ca(OH)$_2$, in organic solvents such as $C_1$ to $C_8$ ethers (tetrahydrofuran, IPE), acetonitrile (ACN), $C_1$ to $C_4$ alcohols (MeOH, EtOH, IPA, propanol, butanol etc.), $C_3$ to $C_8$ ketones or esters (acetone, methyl ethyl ketone, methyl isopropyl ketone, ethyl acetate). The hydrolysis may also be carried out with water, a mixture of the above solvents, or a mixture of water and the above solvents, preferably at room temperature or by heating.

The lactone, particularly for fluvastatin, may be obtained by treating the acid form with an acid such as HCl.

Pharmaceutical Compositions

Pharmaceutical formulations of the present invention contain pharmaceutically acceptable salts or lactone form of the statin with a high syn to anti ratio and/or high purity including substantially free of rosuvastatin triol calcium. Pharmaceutically acceptable salts include those of alkali and alkaline earth metals, preferably calcium. In addition to the active ingredient(s), the pharmaceutical compositions of the present invention may contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®, microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, statin and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets and troches, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

Having thus described the invention with reference to particular preferred embodiments and illustrated it with Examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

EXAMPLES

Example 1

Synthesis of Triol Ester

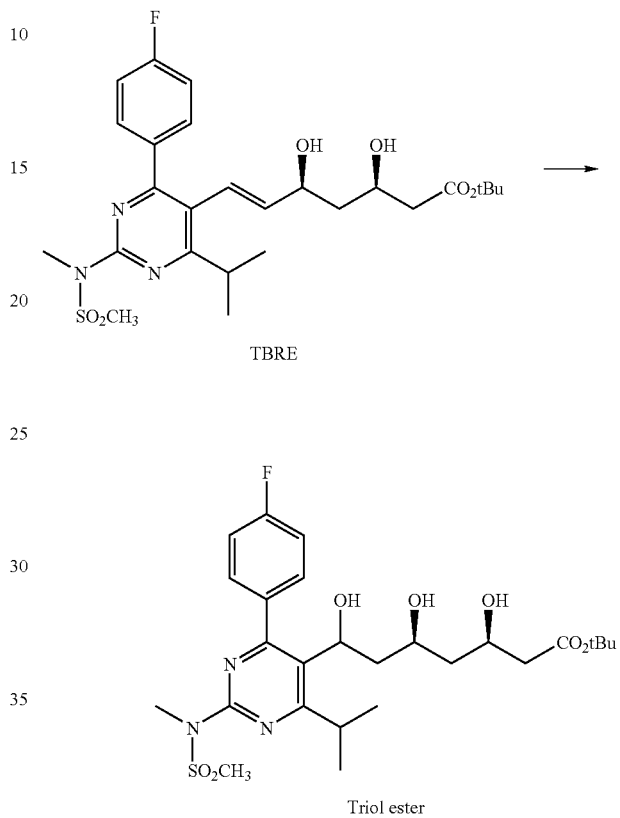

TBRE (10 g) was mixed with 1M solution of borane dimethylsulfide complex in THF (56 ml) in an inert atmosphere. The mixture was stirred for 3 h at 20° C. A solution of NaOH (74 g) in water (5 ml) was slowly added. $H_2O_2$ (30% in water, 15 ml) was added dropwise, so that the temperature of the mixture was kept below 50° C. The mixture was stirred for 0.5 h. A concentrated solution of ammonium chloride (150 ml) was added, and the precipitate was filtered out. The phases were separated and organic phase was first washed with a concentrated solution of sodium sulfite (40 ml), then with a mixture of water (100 ml) and brine (100 ml), and finally with brine (150 ml). Then an organic solvent was removed at reduced pressure, giving a semi-solid residue, containing triol, non-reacted TBRE and some impurities.

Triol was isolated by two chromatographic separations. First separation was performed on an RP-18 column (RediSep® C-18 Reversed Phase Column), using a gradient from 40% to 45% of EtOH in water. The second separation was performed on normal silica column (RediSep® Normal Phase Disposable Column), using a gradient from 0% to 1% of EtOH in $CH_2Cl_2$ as an eluent. Purity 93%. MS (ES+): M+H=556 M+Na+=578

RediSep® is manufactured by Teledyne Isco, Inc (Nebraska).

Example 2

Synthesis of Rosu-Ca-triol

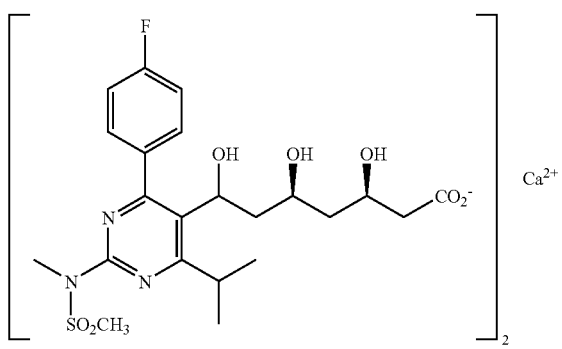

2 g of material, consisting of TBRE and 2.85% triol-ester (3.7 mmole of the carboxylic group) was suspended in EtOH (10 mL)/water (6 mL) mixture. Saturated NaOH solution (0.35 g, 4.1 mmole) was added dropwise at room temperature and the mixture was stirred for 2 h. The solution was concentrated under vacuum to remove EtOH. Calcium salt was precipitated from the water solution by addition of $CaCl_2$ (0.41 g, 3.7 mmole) at 40° C. upon stirring. Stirring was continued for 1 h at room temperature, and the precipitate was filtered, washed with water and dried. The material contained 2.82% Rosu-Ca-triol and 95% Rosu-Ca

Example 3

Synthesis of Rosuvastatin Triol Acid

Rosu triol Ca (0.5 g) is suspended in dichloromethane (5 mL) and HCl (1N in water, 1 mL) is added. After stirring for 15 minutes phases are separated, and organic phase is concentrated in vacuum, giving the residue, which contains mainly the product. It may be additionally purified by column chromatography (silica gel, dichloromethane-methanol mixtures as eluent), giving pure Rosu triol acid.

Example 4

Synthesis of Rosuvastatin Triol Lactone

Rosu triol Ca (4 g) is dissolved in acetonitrile (40 mL) and HCl (1N in water, 40 mL) is added. The mixture is stirred at room temperature overnight. Acetonitrile and water are removed by distillation at reduced pressure. The residue, containing the product, may be additionally purified by flash chromatography (silica gel, hexane-ethyl acetate mixtures as eluent), giving pure rosu triol lactone.

Example 5

Synthesis of Rosuvastatin Triol Calcium 2 g of pure triol-ester (3.7 mmol) is suspended in EtOH (10 mL)/water (6 mL) mixture. Saturated NaOH solution (0.35 g, 4.1 mmole) is added dropwise at room temperature and the mixture is stirred for 2 h. The solution is concentrated under vacuum to remove EtOH. Calcium salt is precipitated from the water solution by addition of $CaCl_2$ (0.41 g, 3.7 mmole) at 40° C. upon stirring. Stirring is continued for 1 h at room temperature, and the precipitate is filtered, washed with water and dried, giving Rosu-Ca-triol.

MS Conditions
Instrument: Bruker Esquir 6000
Source: Positive/Negative switching ESI
Target mass: 556 Da
Compound stability: 50%
Trap drive: 100%
Octopole RF: 195.3 Vpp
Capillary exit: 111.8 V
Drying gas flow rate: 10 L/min
Nebulizer: 60 psig
Drying gas temperature: 365° C.
V cap: 4000 V HPLC Method for Impurity Profile of TBRE

| Column: | C18 | |
|---|---|---|
| Mobile phase | Gradient of Eluent A and Eluent B | |
| Gradient: | Time(min) | Eluent A(%) | Eluent B(%) |
| | 0 | 100 | 0 |
| | 2 | 84 | 16 |
| | 23 | 84 | 16 |
| | 36 | 10 | 90 |
| | 40 | 10 | 90 |
| Eluent A: | 60% 0.005M Ammonium Acetate 40% Acetonitrile:Ethanol = 2:3 | |
| Eluent B: | 100% Acetonitrile:Ethanol = 1:4 | |

UV detection: 243 nm

Run time: 55 min

Flow rate: 0.6 mL/min

Injection volume: 5 L

Column temperature: 5° C.

Discard limit: Less than 0.02%

Sample preparation: 0.5 mg/mL

RT of TBRE: about 24.5 min

RRT of Triol—TBRE impurity is 0.6 corresponding to the main peak of TBRE.

HPLC Method for Impurity Profile of ROSU

| Column: | C18 | | |
|---|---|---|---|
| Mobile phase | Gradient of Eluent A, Eluent B and Eluent C | | |
| Gradient: | Time(min) | Eluent A(%) | Eluent B(%) | Eluent C(%) |
| | 0 | 100 | 0 | 0 |
| | 15 | 0 | 100 | 0 |
| | 20 | 0 | 93 | 7 |
| | 30 | 0 | 78 | 22 |
| | 40 | 0 | 5 | 95 |
| | 45 | 0 | 5 | 95 |
| Eluent A: | 60% 0.05% Acetic acid glacial pH 3.5 with Ammonium hydroxide 35% Acetonitrile 5% Ethanol | | |
| Eluent B: | 55% 0.05% Acetic acid glacial pH 3.5 with Ammonium hydroxide 45% Acetonitrile | | |
| Eluent C: | 100% Ethanol | | |

UV detection: 243 nm

Run time: 45 min

Flow rate: 0.5 mL/min

Injection volume: 10 μL

Column temperature: 20° C.

Discard limit: Less than 0.02%

Sample preparation: 0.2 mg/mL

RT of ROSU: about 19 min

RRT of Triol —ROSU impurity is 0.7 corresponding to the main peak of ROSU.

FIG. 1

Example 6

Reduction of FKE-tBu to FDE-tBu

A 1 L triple-jacket reactor, covered with aluminum foil was loaded with FKE-tBu (30 g), THF (Tetrahydrofuran) (CP, 300 ml) and Methanol (CP, 60 ml). The solution was cooled to (−70° C.) and then BM-9-BBN (1M solution in Hexanes, 71 ml.) was added. The mixture was stirred at (−70° C.) for 30 minutes. Sodium borohydride (2.4 g) was added and the reaction mixture was stirred at (−70° C.) for about 2 hours (monitoring by HPLC for the consumption of FKE-tBu). A solution of 30% Hydrogen peroxide (48 ml) was added and the reaction mixture was allowed to stir at room temperature for 19.5 hours. The reaction mixture was diluted with EtOAc (ethyl acetate) (150 ml), water (150 ml) and Brine (105 ml). The phases were separated and the organic layer was washed with saturated solution of $NaHCO_3$ (1×120 ml), saturated solution of $Na_2SO_3$ (1×120 ml) and Brine (1×120 ml). The organic layer was evaporated under vacuum to dryness.

The obtained solid residue was dissolved in acetone (90 ml) at reflux temperature while the flask was covered with aluminum foil. Then n-Heptane (210 ml) was added at reflux. The mixture was cooled to room temperature and stirred at this temperature for about 18 hours. The product was isolated by filtration under nitrogen atmosphere, washed with n-Heptane (100 ml) and dried at 40° C. in a vacuum oven for 24 hours to obtain 21.9 g (73%) of FDE-tBu crude. First crystallization-Syn:anti-99.0/0.45.

Example 7

Crystallization of Crude FLV-Diol Ester from Acetone and n-Heptane

FDE-tBu crude (syn:anti 99.0:0.45) was dissolved in Acetone (116 ml) at reflux temperature while the flask was covered with aluminum foil. Then n-Heptane (252 ml) was added at reflux. The mixture was cooled to 37° C. during 1 hour, stirred at this temperature for 1 hour and cooled to 20° C. during 1 hour. The obtained slurry was stirred at 20° C. for 15 hours. The product was isolated by filtration under nitrogen atmosphere, washed with n-Heptane (3×66 ml) and dried at 40° C. in a vacuum oven for 24 hours to obtain 18.9 g (90%) of FDE-tBu cryst (syn:anti 99.8:0.17).

Example 8

Conversion of FDE-tBu to FLV Na Form XIV

Water (56 ml), ACN (Acetonitrile) (200 ml) and FDE-tBu (40 gr) are added to a 1 L stirred reactor. At 25 deg. 7.5 gr of 47% NaOH solution are added and the mixture is heated to 35° C. The mixture becomes clear during the hydrolysis. End of reaction is determined by HPLC (~3-4 hr). The mixture is then cooled to 25° C. ACN (Acetonitrile) (600 ml) is added to the mixture causing precipitation of FLV Na crystals. The mixture is stirred for ~5 hr and then filtered under vacuum. The wet product is washed with 120 ml of ACN (Acetonitrile). The wet product is dried in a vacuum oven at 40° C. to obtain FLV Na form XIV crystals. Yield: 87%

Example 9

Conversion of FDE-Me to FLV Na

Fluvastatin-diol methyl ester (3.0 g) was added to solution of NaOH (1 eq.) in water (0.75 ml) and ethanol (7.5 ml). The mixture was heated to reflux and stirred until the raw material wasn't observed by HPLC. After this time 58 ml of MTBE were dripped to the solution during 1.5 hr. Turbidity appeared in the solution, which was cooled slowly to room temperature and stirred over night. The product was isolated by filtration under nitrogen, washed with MTBE (50 ml) and dried at 50° C. in a vacuum oven for 24 hours to obtain 2.21 grams (72.3%) of fluvastatin sodium.

Example 10

Conversion of FDE-ME to FLV Na

Fluvastatin-diol-methyl ester (FDE-ME) (4.0 g) was dissolved in acetone (40 ml). A solution of NaOH (0.38 gr) in MeOH (4 ml) was added and the mixture was stirred at room temperature for 20 hr. The product was isolated by filtration under nitrogen, washed with acetone (20 ml) and dried at 50° C. in a vacuum oven for 26 hours to obtain 3.35 gr (82.2%) of fluvastatin sodium.

Example 11

Crystallization of Crude FLV-Diol Ester from IPA

Crude FLV-diol-tert butyl ester (that prepared as mentioned in the reduction procedure with BM-9-BBM) (5.77 gr, Syn:anti-98.6/0.88) was dissolved in IPA (60 ml) by heating to reflux. After 30 minutes, the clear solution was cooled to room temperature and stirred over night. The solution was then concentrated (approximately 17 ml of IPA was evaporated) and stirred at room temperature overnight. The product was isolated by vacuum filtration under nitrogen flow, washed with IPA (30 ml), then dried in vacuum oven at 40° C. for to obtain FLV-diol-tert butyl ester. First crystallization-Syn:anti-98.9/0.61.

Example 12

Crystallization of Crude FLV-Diol Ester from Acetone

Crude FLV-diol-t-Butyl ester (4.0 g) was dissolved in acetone (18.5 ml) at reflux temperature. After 45 minutes the clear solution was cooled to room temperature to obtain a massive precipitate. The suspension was diluted with Acetone (10 ml) and the product was isolated by vacuum filtration under nitrogen flow, washed with Acetone (4×10 ml) and dried in a vacuum oven at 50° C. for 24 hours to obtain FLV-diol-t-Butyl ester (1.7 g, 42%). First crystallization-Syn: anti-98.8/0.27; Second crystallization-Syn:anti-99.6/0.04.

Example 13

Crystallization of Crude FLV-Diol Ester from Isobutylacetate

FDE-tBu (3 gr) (Syn:anti-98.6/0.88) was dissolved in Isobutylacetate (48 ml) by reflux. The solution was cooled to room temperature and stirred over night. The product was isolated by vacuum filtration, washed with isobutylacetate and dried in vacuum oven at 50° C. for 24 hours to obtain FDE-tBu (1.92 gr, 64% yield). First crystallization-Syn:anti-99.6/0.2.

Example 14

Crystallization of Crude FLV-Diol Ester from IPA and MTBE

FDE-tBu (3 gr, syn:anti 98.6:0.88) was dissolved in IPA (15 ml) by reflux and MTBE (30 ml) was added. The solution was cooled to room temperature and stirred over night. The product was isolated by vacuum filtration, washed with a solution of MTBE:IPA 1:1 v:v (20 ml) and dried in vacuum oven at 40 deg for 24 hours to obtain FDE-tBu (1.5 gr, 51% yield). Syn:anti 99.6:0.20

Example 15

Reduction of TB-21 to TB-22 (tBu-Rosuvastatin) with B—OMe-9-BBN and $NaBH_4$

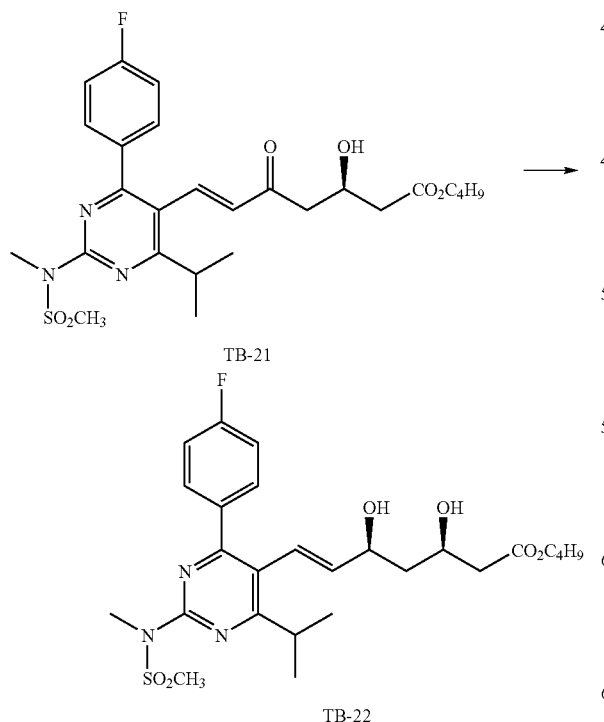

A 100 mL 3-necked flask equipped with a mechanical stirrer, rubber septum, and nitrogen bubbler was charged with TB-21 (1.0 g), tetrahydrofuran (47 mL) and methanol (13.5 mL). The mixture was stirred at room temperature until all TB-21 was dissolved. The reaction mixture was then cooled to −78° C. B—OMe-9-BBN (2.05 mL, 1M in Hexanes) was added via a syringe at −78° C. and the solution was stirred for about 30 minutes. $NaBH_4$ (0.078 g) was added at −78° C. and the solution was stirred for about 3 hours. $H_2O_2$ (0.8 mL, 30% in water) was added at −78° C. The solution was then allowed to reach room temperature and the solution was evaporated to dryness. Ethyl acetate (5 mL), water (5 mL) and NaCl (saturated, 3.5 mL) was added to the residue. The organic phase was separated and washed with saturated $NaHCO_3$ (4 mL), saturated $Na_2SO_3$ (4 mL), and saturated NaCl (4 mL). The combined organic layers were concentrated under reduced pressure to obtain a residue of the diol TB-22. (1.19 g, 92.0%). Diastereoisomer content is 0.37%.

Example 16

Crystallization of TBRE (TB22) from Toluene

TBRE (2 g, 0.23% diastereoisomers) was dissolved in Toluene (7 ml) by heating to approximately 60° C. The solution was then allowed to cool to room temperature, and was cooled afterwards in an ice bath to 0° C. The resulting mixture was stirred at this temperature overnight. The solid was then filtered under reduced pressure, washed, and dried at 50° C. under reduced pressure for 18 hrs to get 1.59 g of TBRE (0.08% diastereoisomers).

Example 17

Slurry TBRE in MeOH

TBRE (1 g, 1.1% of diastereoisomers) was suspended in MeOH (5 ml) while stirring at ambient temperature overnight. The solid was then filtered under reduced pressure, washed, and dried at 45° C. under atmospheric pressure for 18 hrs to obtain 0.60 g of TBRE (diastereoisomers 0.51%)

Example 18

Preparation of Rosuvastatin Calcium from Rosuvastatin Ester

A 1000 ml reactor equipped with a mechanical stirrer was charged with EtOH (100 mL) water (60 ml) t-Butyl-Rosuvastatin (20 g) and $NaBH_4$ (0.1 g). To this suspension, NaOH 47% 1.1 eq (3.5 g) was added dropwise at 25±5° C. and the mixture was stirred at 25±5° C. for two hours. The mixture was then filtered under reduced pressure with a Sinter to eliminate the active carbon present in the solution.

To this suspension water (140 ml) was added and the reaction mixture was acidified with HCl 0.1M until PH 8-10. The mixture was then washed with Toluene (100 ml) and stirred at 25±5° C. for half an hour. The aqueous layer was isolated. To the aqueous phase active carbon was added and the suspension was stirred at 25±5° C. for 30 min. The mixture was filtered under reduced pressure with Sinter and Hyflo to eliminate the active carbon present in the solution. Thereafter the reaction mixture was concentrated under reduced pressure at 40° C. to half the solution volume.

Make-up of the solution was performed to 10 volumes of water versus TBRE. The solution was heated to 40-45° C. CaCl$_2$ (4.13 g) was added dropwise to this solution over 30-90 min at 38-45° C. The suspension was then cooled to 25±5° C., stirred at 25±5° C. for 1 hr, filtered and washed with water (4×20 ml) to get a powdery compound (17.3 g dry, 92%).

The resulting solution was placed in a flask and heated to 40° C. Solid CaCl$_2$ (0.25 g) was added portionwise to this solution while stirring. The resulting mixture was then cooled to 25±5° C., stirred at 25±5° C. for 1 hr, filtered and washed with water to get a powdery product, which was dried in vacuum at 50° C.

HPLC Method for Diastereomer Content in Tert-Butyl Ester of Rosuvastatin

HPLC Conditions:

Column—BDS Hypersil C18

Mobile phase—Gradient of Buffer and Organic modifier

Buffer—Ammonium acetate buffer

Organic modifier—Acetonitrile and Ethanol

Detection—UV-245 nm

Injection—10 µl

Column temperature—5° C.

Diluent—Acetonitrile/Water

Sample Preparation:

0.5 mg/ml in diluent

Calculations:

$$\% \; 3R, 5R - \text{isomer} = \frac{\text{Area } 3R, 5R - \text{isomer in } smp. \times 100\%}{\sum \text{all Areas}}$$

HPLC Method for Diastereomer Content in Rosuvastatin Ca

HPLC Conditions:

Column—C18

Mobile phase—Gradient of Buffer and Organic modifier

Buffer—Ammonium acetate buffer

Organic modifier—Acetonitrile and Ethanol

Detection—UV-243 nm

Injection—10 µl

Column temperature—20° C.

Diluent—Acetonitrile/Buffer

Sample preparation: 0.2 mg/ml in diluent

Calculations:

$$\% \; 3R, 5R - \text{isomer} = \frac{\text{Area } 3R, 5R - \text{isomer in } smp. \times 100\%}{\sum \text{all Areas}}$$

What is claimed is:

1. A rosuvastatin triol having the following structure:

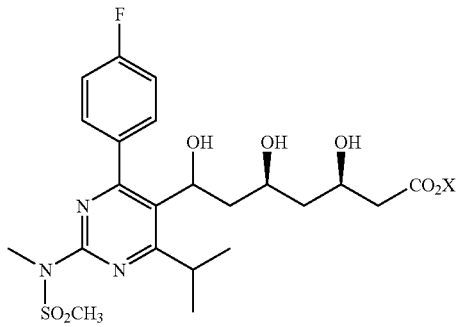

wherein X is a hydrogen, an alkali or alkaline earth metal, or a $C_1$-$C_4$ alkyl group.

2. The rosuvastatin triol of claim 1, wherein the rosuvastatin triol is isolated.

3. The rosuvastatin triol of claim 1, wherein the rosuvastatin triol is substantially free from corresponding rosuvastatin diol.

4. The rosuvastatin triol of claim 1 in acid form having the following structure:

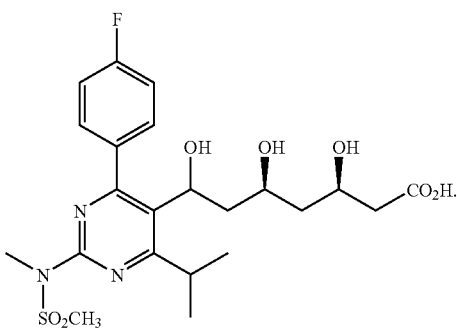

5. The rosuvastatin triol of claim 4, wherein the rosuvastatin triol is isolated.

6. The rosuvastatin triol of claim 4, wherein the rosuvastatin triol is substantially free from corresponding rosuvastatin diol.

7. The rosuvastatin triol of claim 1 in ester form having the following structure:

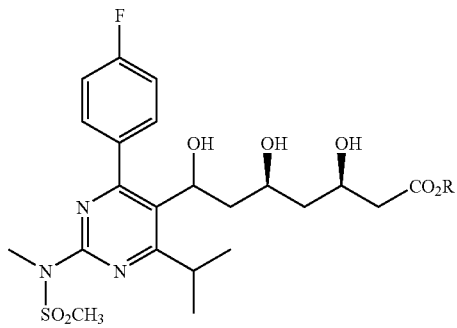

wherein R represents a $C_{1-4}$ alkyl.

8. The rosuvastatin triol of claim 7, wherein the rosuvastatin triol ester is isolated.

9. The rosuvastatin triol of claim 7, wherein the rosuvastatin triol ester is substantially free from corresponding rosuvastatin diol ester.

10. The rosuvastatin triol of claim 7, wherein the ester is a tert-butyl ester.

11. The rosuvastatin triol of claim 1, in salt form having the following structure:

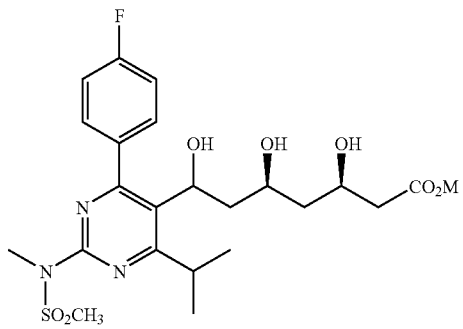

wherein M represents an alkali or alkaline earth metal cation.

12. The rosuvastatin triol of claim 11, wherein the metal cation is an alkaline earth metal with two molecules of rosuvastatin present for each cation.

13. The rosuvastatin triol of claim 12, wherein the metal cation is Ca2+.

14. The rosuvastatin triol of claim 11, wherein the rosuvastatin triol is isolated.

15. The rosuvastatin triol of claim 11, wherein the rosuvastatin triol is substantially free from corresponding rosuvastatin diol.

16. Rosuvastatin triol of claim 1 in lactone form having the following structure:

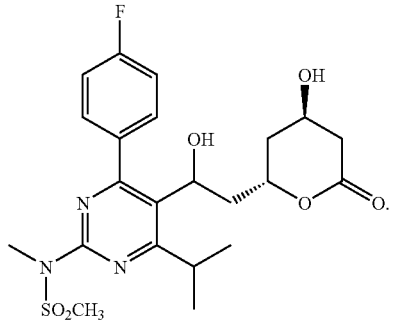

17. The rosuvastatin triol of claim 16, wherein the rosuvastatin triol lactone is isolated.

18. The rosuvastatin triol of claim 16, wherein the rosuvastatin triol lactone is substantially free from corresponding rosuvastatin diol.

19. The rosuvastatin triol of claim 1, wherein the rosuvastatin triol is selected from the group consisting of: rosuvastatin triol in (7S) form; rosuvastatin triol in (7R) form; and epimeric rosuvastatin triol.

20. A process for preparing the triol of claim 7 comprising oxidizing rosuvastatin diol $C_1$ to $C_4$ ester to obtain the rosuvastatin triol ester with a hydroxyl group at position 7.

21. The process of claim 20, wherein the process comprises combining rosuvastatin $C_1$-$C_4$ ester with a solution of a borane in an organic solvent to obtain a reaction mixture, combining the resulting reaction mixture with a solution of an inorganic base in water, and adding peroxide and recovering the triol ester.

22. The process of claim 20, wherein the borane is a borane complex of dimethylsulfide.

23. The process of claim 22, wherein the borane is a monoalkyl- or dialkyl-borane.

24. The process of claim 21, wherein the peroxide is $H_2O_2$.

25. The process of claim 21, wherein the peroxide is t-Butyl Hydroperoxide (TBHP) or Magnesium monoperoxyphthalate hexahydrate (MMPP).

26. The process of claim 21, wherein the base is an inorganic base.

27. The process of claim 26, wherein inorganic base is an alkali metal base.

28. The process of claim 27, wherein the base is a hydroxide base.

29. The process of claim 28, wherein the hydroxide base is NaOH, KOH or LiOH.

30. The process of claim 21, wherein the base is $NH_4OH$.

31. The process of claim 21, wherein the organic solvent is a $C_3$-$C_8$ ether.

32. The process of claim 31, wherein the organic solvent is tetrahydrofuran.

33. A process for preparing the triol salt of claim 11 comprising suspending the triol ester of the following formula:

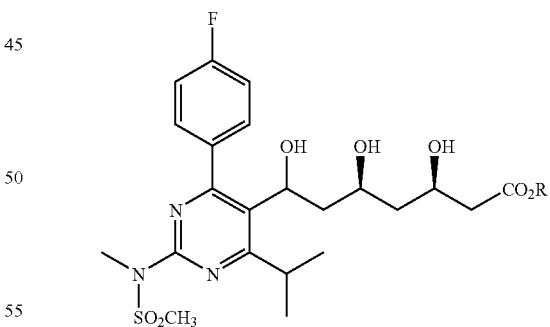

wherein R is a $C_1$-$C_4$ ester, in a mixture of water and an organic solvent, and combining the suspension with a base and a source of ions.

34. The process of claim 33, wherein the organic solvent is a $C_1$-$C_4$ alcohol.

35. The process of claim 33, wherein the organic solvent is ethanol.

36. The process of claim 33, wherein the source of ions is calcium chloride.

37. A process for preparing the triol acid of claim 4 comprising contacting the rosuvastatin triol salt of the following formula:

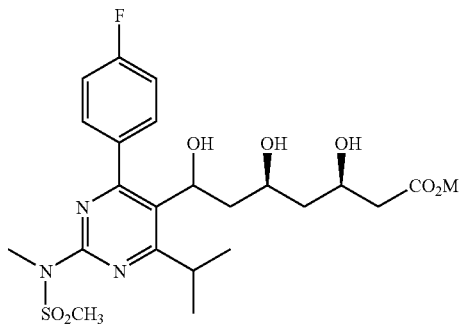

with an acid, wherein M is an alkali or alkaline earth metal.

38. The process of claim 37, wherein the acid is hydrochloric or sulfuric acid.

39. The process of claim 37, wherein rosuvastatin triol salt is combined with an organic solvent.

40. The process of claim 39, wherein the organic solvent is dichloromethane.

41. A process for preparing rosuvastatin triol acid of claim 4 comprising hydrolyzing an ester of the following formula:

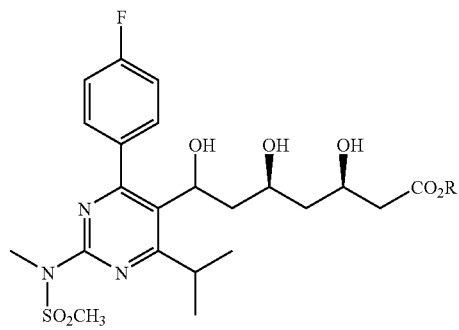

with an acid, wherein R is a $C_1$-$C_4$ ester.

42. The process of claim 41, wherein the acid is HCl or $H_2SO_4$.

43. A process for preparing the lactone of any one of claims claim 16-19, comprising hydrolyzing the triol ester of the following formula:

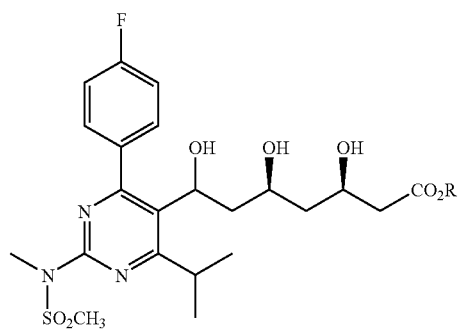

wherein R is a $C_1$-$C_4$ ester, and converting the hydrolyzed ester to a lactone.

44. A process for preparing rosuvastatin triol salt of claim 11 with the following structure:

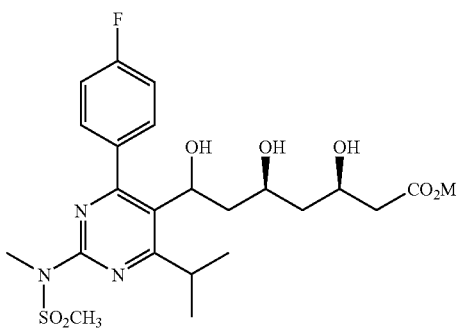

comprising hydrolyzing a lactone having the following structure

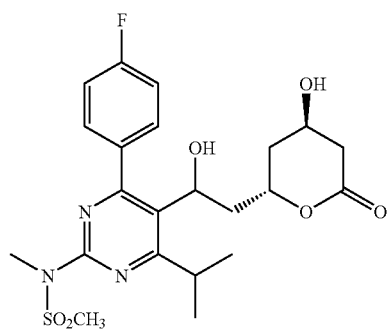

and converting the hydrolyzed lactone to an the salt, wherein M is alkali metal or an alkaline earth metal.

45. A process for preparing a rosuvastatin triol salt with the following structure:

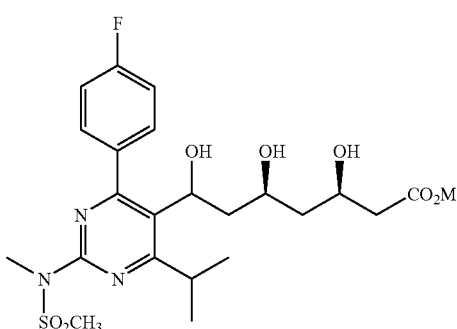

comprising contacting an acid with the following structure

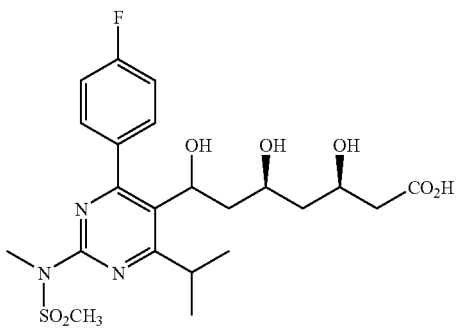

with a base wherein M represents an alkali or alkaline earth metal cation.

46. A process for reducing the amount of impurities present in a pharmaceutical composition of rosuvastatin calcium comprising measuring the amount of rosuvastatin triol calcium in batches of rosuvastatin diol calcium, selecting batches of the rosuvastatin diol calcium with desirable level of the rosuvastatin triol calcium and preparing pharmaceutical compositions with the selected rosuvastatin diol batch.

47. A process for reducing the amount of rosuvastatin triol ester present in a mixture comprising rosuvastatin diol ester and rosuvastatin triol ester comprising measuring the amount of rosuvastatin triol $C_1$-$C_4$ ester in batches of rosuvastatin diol $C_1$-$C_4$ ester, selecting batches of the rosuvastatin diol $C_1$-$C_4$ ester with the triol $C_1$-$C_4$ ester and preparing pharmaceutical compositions of rosuvastatin diol calcium with the selected rosuvastatin diol $C_1$-$C_4$ ester batch.

48. A method of determining the amount of an impurity in a sample of rosuvastatin diol ester comprising measuring by GC or HPLC the area under a peak corresponding to rosuvastatin triol ester in a reference standard that comprises a known amount of rosuvastatin triol ester; measuring by HPLC or GC the area under a peak corresponding to rosuvastatin triol ester in a sample comprising rosuvastatin triol and rosuvastatin diol esters; and determining the amount of the triol ester in the sample by comparing the area of reference standard with that of the test sample.

49. The method of claim 48, wherein the triol ester is a t-butyl ester.

50. A method of determining the amount of an impurity in a sample of rosuvastatin calcium comprising measuring by GC or HPLC the area under a peak corresponding to rosuvastatin triol calcium in a reference standard comprising a known amount of rosuvastatin triol calcium; measuring by GC or HPLC the area under a peak corresponding to rosuvastatin triol calcium in a sample comprising rosuvastatin triol and rosuvastatin diol calcium salts; and determining the amount of the triol calcium in the sample by comparing the area of reference standard with that of the test sample.

51. A method of identifying the relative retention time (RRT) of an impurity in a sample of rosuvastatin diol ester comprising measuring by GC or HPLC the relative retention time (RRT) corresponding to rosuvastatin triol ester in a reference marker sample; carrying out GC or HPLC with a test sample comprising of the rosuvastatin diol ester and rosuvastatin triol ester to obtain an GC or HPLC chromatogram with retention times; and identifying the relative retention time (RRT) of the triol ester in the sample by comparing the relative retention time (RRT) of the reference marker to the relative retention time (RRT) of the test sample.

52. The method of claim 51, wherein the triol ester is a t-butyl ester.

53. A method of identifying the relative retention time (RRT) of an impurity in a sample of rosuvastatin diol calcium comprising measuring by GC or HPLC the relative retention time (RRT) corresponding to rosuvastatin triol calcium in a reference marker sample; carrying out GC or HPLC with a test sample comprising of the rosuvastatin diol and rosuvastatin triol calcium salts to obtain an HPLC chromatogram with retention times; and identifying the relative retention time (RRT) of the triol calcium in the sample by comparing the relative retention time (RRT) of the reference marker to the relative retention time (RRT) of the test sample.

* * * * *

UNITED STATES PATENT AND TRADEMARK OFFICE
CERTIFICATE OF CORRECTION

| | | |
|---|---|---|
| PATENT NO. | : 7,851,624 B2 | Page 1 of 1 |
| APPLICATION NO. | : 12/075848 | |
| DATED | : December 14, 2010 | |
| INVENTOR(S) | : Niddam-Hildesheim et al. | |

It is certified that error appears in the above-identified patent and that said Letters Patent is hereby corrected as shown below:

At column 35, line 36, change "$Ca2_+$." to -- $Ca^{2+}$ --

At column 36, line 7, change "$C_1$ to $C_4$" to -- $C_1$ - $C_4$ --

At column 36, line 23, change "Hydroperoxide" to -- hydroperoxide --

Signed and Sealed this
Fifth Day of July, 2011

David J. Kappos
*Director of the United States Patent and Trademark Office*